United States Patent
Tabuchi et al.

(10) Patent No.: US 11,896,688 B2
(45) Date of Patent: Feb. 13, 2024

(54) W/O EMULSION COMPOSITION

(71) Applicant: KAO CORPORATION, Tokyo (JP)

(72) Inventors: Sho Tabuchi, Chigasaki (JP); Seri Akiyama, Odawara (JP); Hidetoshi Taima, Machida (JP)

(73) Assignee: KAO CORPORATION, Tokyo (JP)

(*) Notice: Subject to any disclaimer, the term of this patent is extended or adjusted under 35 U.S.C. 154(b) by 345 days.

(21) Appl. No.: 16/972,808

(22) PCT Filed: Jun. 11, 2019

(86) PCT No.: PCT/JP2019/023060
§ 371 (c)(1),
(2) Date: Dec. 7, 2020

(87) PCT Pub. No.: WO2019/240119
PCT Pub. Date: Dec. 19, 2019

(65) Prior Publication Data
US 2021/0259929 A1    Aug. 26, 2021

(30) Foreign Application Priority Data

Jun. 12, 2018  (JP) .................. 2018-112290
Jun. 12, 2018  (JP) .................. 2018-112291
Jun. 7, 2019   (JP) .................. 2019-106807

(51) Int. Cl.
| | |
|---|---|
| *A61K 8/06* | (2006.01) |
| *A61K 8/37* | (2006.01) |
| *A61K 8/34* | (2006.01) |
| *A61K 8/68* | (2006.01) |
| *A61K 8/894* | (2006.01) |
| *A61Q 19/00* | (2006.01) |

(52) U.S. Cl.
CPC .............. *A61K 8/064* (2013.01); *A61K 8/342* (2013.01); *A61K 8/37* (2013.01); *A61K 8/68* (2013.01); *A61K 8/894* (2013.01); *A61Q 19/00* (2013.01); *A61K 2800/5422* (2013.01); *A61K 2800/596* (2013.01)

(58) Field of Classification Search
None
See application file for complete search history.

(56) References Cited

U.S. PATENT DOCUMENTS

2010/0055220 A1    3/2010   Akatsuka et al.

FOREIGN PATENT DOCUMENTS

| | | |
|---|---|---|
| EP | 0 391 124 A2 | 10/1990 |
| JP | 3-47108 A | 2/1991 |
| JP | 2006-273747 A | 10/2006 |
| JP | 2010-513221 A | 4/2010 |
| JP | 2013-53145 A | 3/2013 |
| JP | 2016-104730 A | 6/2016 |
| JP | 2016-108270 A | 6/2016 |
| JP | 2016104730 A * | 6/2016 |
| JP | 2016108270 A * | 6/2016 |
| JP | 2019-21 4527 A | 12/2019 |

OTHER PUBLICATIONS

English language translation of JP 2016-108270 A. (Year: 2016).*
English language translation of JP 2016 104730 A. (Year: 2016).*
International Search Report dated Sep. 17, 2019 in PCT/JP2019/023060 filed Jun. 11, 2019, 1 page.
Extended European Search Report dated Feb. 7, 2022 in European Patent Application No. 19819722.0, 8 pages.

* cited by examiner

*Primary Examiner* — Dominic Lazaro
(74) *Attorney, Agent, or Firm* — Oblon, McClelland, Maier & Neustadt, L.L.P.

(57) ABSTRACT

A W/O emulsion composition having excellent storage stability under temperature cycle conditions is provided. A W/O emulsion composition including the following components (A), (B), (C), (D) and (E): (A) a glycerol monofatty acid ester having 12 to 26 carbon atoms; (B) a higher alcohol having 10 to 22 carbon atoms; (C) a ceramide; (D) one or more selected from the group consisting of sphingosine, a salt thereof and an ionic surfactant; and (E) a nonionic surfactant including the following (e1) and (e2): (e1) one or more selected from the group consisting of a crosslinked polyether-modified silicone and a crosslinked polyglycerol-modified silicone and (e2) one or more selected from the group consisting of a polyether-modified silicone, a polyglycerol-modified silicone and a polyglycerol fatty acid ester.

15 Claims, No Drawings

W/O EMULSION COMPOSITION

CROSS REFERENCE TO RELATED APPLICATION

This application is a national stage entry under 35 USC 371 of PCT/JP2019/023060, filed on Jun. 11, 2019, and claims priority to Japanese Patent Applications No. 2018-112290 filed on Jun. 12, 2018, No. 2018-112291 filed on Jun. 12, 2018, and No. 2019-106807, filed on Jun. 7, 2019.

FIELD OF THE INVENTION

The present invention relates to a W/O emulsion composition.

BACKGROUND OF THE INVENTION

Ceramides, a kind of sphingolipids, occur in the cell membrane at high concentration. Ceramides are known to be a key component in stratum corneum intercellular lipid and constitute a lipid barrier in the skin, playing an important role of keeping the skin soft and fresh. Since ceramides increase water-retaining power of the stratum corneum as one of the measures to improve rough skin, they are an effective component in an external agent for the skin.

Such ceramides are highly crystalline and their stable mixing in an emulsion system is difficult. Thus, an O/W/O emulsion cosmetic prepared by dispersing an O/W emulsion composition containing a ceramide and phospholipid in an oil phase containing a silicone surfactant (Patent Literature 1); a technique of first preparing an O/W emulsion of a ceramide and then adding liquid oil and fat and a lipophilic emulsifier thereto to prepare a double emulsion cosmetic composition composed of an O/W/O emulsified product (Patent Literature 2); and an external agent for the skin in the form of a water-in-oil emulsion, containing a ceramide, an organic-modified clay mineral, diester of N-acylglutamic acid and phytosterol (Patent Literature 3) have been reported. Furthermore, an O/W/O external agent for the skin containing a ceramide, a glycerol monofatty acid ester, a higher alcohol, a sphingosine salt or an ionic surfactant has been reported (Patent Literature 4).

Patent Literature 1: JP-A-2006-273747
Patent Literature 2: JP-A-H03-47108
Patent Literature 3: JP-A-2010-513221
Patent Literature 4: JP-A-2016-104730

SUMMARY OF THE INVENTION

The present invention provides a W/O emulsion composition containing the following components (A), (B), (C), (D) and (E):
(A) a glycerol monofatty acid ester having 12 to 26 carbon atoms;
(B) a higher alcohol having 10 to 22 carbon atoms;
(C) a ceramide;
(D) one or more selected from the group consisting of sphingosine, a salt thereof and an ionic surfactant; and
(E) a nonionic surfactant containing the following (e1) and (e2):
(e1) one or more selected from the group consisting of a crosslinked polyether-modified silicone and a crosslinked polyglycerol-modified silicone; and
(e2) one or more selected from the group consisting of a polyether-modified silicone, a polyglycerol-modified silicone and a polyglycerol fatty acid ester.

DETAILED DESCRIPTION OF THE INVENTION

In the O/W/O external agent for the skin described in Patent Literature 4, crystallization of a ceramide in low temperature storage is suppressed, and thus the agent has emulsification stability and has excellent skin-protecting feeling and smoothness when applied to the skin. However, when the product is brought into the market, further improvement of storage stability is required under temperature cycle conditions possibly occurring in the distribution process.

Thus, the present invention provides a W/O emulsion composition containing a ceramide having excellent storage stability under temperature cycle conditions and excellent feeling on use when applied to the skin.

Then, the present inventors studied the O/W/O external agent for the skin containing a ceramide described in Patent Literature 4, and found that including two specific types of nonionic surfactant together provides a W/O emulsion composition having excellent storage stability under temperature cycle conditions and excellent feeling on use when applied to the skin, and completed the present invention.

The W/O emulsion composition of the present invention has excellent stability of the emulsion system even after stored in temperature cycles and has excellent feeling on use such as thickness and good spreadability when applied to the skin.

DESCRIPTION OF EMBODIMENTS

The W/O emulsion composition of the present invention contains the following components (A) to (E):
(A) a glycerol monofatty acid ester having 12 to 26 carbon atoms;
(B) a higher alcohol having 10 to 22 carbon atoms;
(C) a ceramide;
(D) one or more selected from the group consisting of sphingosine, a salt thereof and an ionic surfactant; and
(E) a nonionic surfactant containing the following (e1) and (e2):
(e1) one or more selected from the group consisting of a crosslinked polyether-modified silicone and a crosslinked polyglycerol-modified silicone; and
(e2) one or more selected from the group consisting of a polyether-modified silicone, a polyglycerol-modified silicone and a polyglycerol fatty acid ester.

(Component (A))

The component (A) is a glycerol monofatty acid ester having 12 to 26 carbon atoms.

The number of carbon atoms of the component (A) is preferably 14 or more and more preferably 16 or more, and preferably 24 or less and more preferably 22 or less in order to suppress precipitation of the component (C) described later and provide excellent feeling on use.

Specific examples of the component (A) include glycerol monolaurate, glycerol monomyristate, glycerol monopalmitate, glycerol monostearate, glycerol monobehenate, glycerol monooleate, glycerol monoisostearate, glycerol monoarachidate and glycerol monolinolate. Of them, from the above perspective, one or more selected from the group consisting of glycerol monobehenate, glycerol monostearate and glycerol monopalmitate is preferred, and glycerol monobehenate is more preferred.

In the present embodiment, one component (A) may be used, or two or more of them may be used in combination. In the present embodiment, the content of the component (A) in the emulsion composition is preferably from 0.05 to 12% by mass, more preferably from 0.2 to 10% by mass, further preferably from 0.2 to 7% by mass, still more preferably from 0.2 to 4% by mass, yet more preferably from 0.3 to 2% by mass, still further preferably from 0.3 to 1.0% by mass and yet further preferably from 0.4 to 0.8% by mass based on the whole emulsion composition to improve emulsification stability of the emulsion composition, suppress friction feeling when applied, and improve skin-protecting feeling.

(Component (B))

The component (B) is a higher alcohol having 10 to 22 carbon atoms.

The number of carbon atoms of the component (B) is preferably 14 or more and more preferably 16 or more, and preferably 20 or less and more preferably 18 or less in order to suppress precipitation of the component (C) described later and provide excellent feeling on use.

In the present embodiment, one component (B) may be used, or two or more of them may be used in combination. In the present embodiment, specific examples of component (B) include monovalent alcohol such as myristyl alcohol, cetyl alcohol, stearyl alcohol, behenyl alcohol and oleyl alcohol. Of them, those having a linear alkyl group are preferred, and one or more monovalent alcohols having 16 to 18 carbon atoms selected from cetyl alcohol and stearyl alcohol is more preferred.

In the present embodiment, the content of the component (B) in the emulsion composition is preferably from 0.05 to 15% by mass, more preferably from 0.2 to 10% by mass, further preferably from 0.2 to 7% by mass, still more preferably from 0.2 to 4% by mass, yet more preferably from 0.3 to 2% by mass, still further preferably from 0.3 to 1.0% by mass, yet further preferably from 0.4 to 0.8% by mass based on the whole emulsion composition to improve emulsification stability of the emulsion composition, suppress stickiness when applied, and improve thickness and skin-protecting feeling when applied.

Furthermore, in the emulsion composition of the present embodiment, the total content of the components (A) and (B), i.e., the mass ratio represented by ((A)+(B)), is preferably from 0.15 to 10% by mass, more preferably from 0.4 to 0% by mass, further preferably from 0.6 to 3% by mass, and yet more preferably from 0.7 to 2.5% by mass, and particularly preferably from 0.8 to 2.0% by mass based on the whole emulsion composition to improve emulsification stability of the emulsion composition.

Furthermore, the mass ratio of the component (A) to the component (B), ((A)/(B)), is preferably 0.1 or more, more preferably 0.4 or more, further preferably 0.6 or more to improve thickness and skin-protecting feeling when the emulsion composition is applied. The mass ratio is preferably 5 or less, more preferably 3.0 or less, and further preferably 2.5 or less to improve skin-protecting feeling and reduce friction feeling when applied.

(Component (C))

The component (C) is a ceramide, and one or more selected from the group consisting of natural ceramides and pseudo-ceramides may be used. More specifically, ceramides described in JP-A-2013-53146 may be used.

Specific examples of natural ceramides include ceramide Types 1 to 7 which are amidated products of sphingosine, dihydrosphingosine, phytosphingosine, or sphingadienine (e.g., swine and human ceramides described in FIG. 2 of J. Lipid Res., 24: 759 (1983) and FIG. 4 of J. Lipid. Res., 35: 2069(1994)).

The examples also include N-alkyl forms (e.g., N-methyl forms) thereof.

For these ceramides, natural optically active forms (D(−) forms), unnatural optically active forms (L(+) forms) and a mixture of a natural form and an unnatural form may be used. The relative configurations of the above compounds may be ones of natural type or unnatural type other than those, or of mixed type. Of them, CERAMIDE 1, CERAMIDE 2, CERAMIDE 3, CERAMIDE 5 CERAMIDE 6II compounds (INCI, 8th Edition) and those represented by the following formula are preferred.

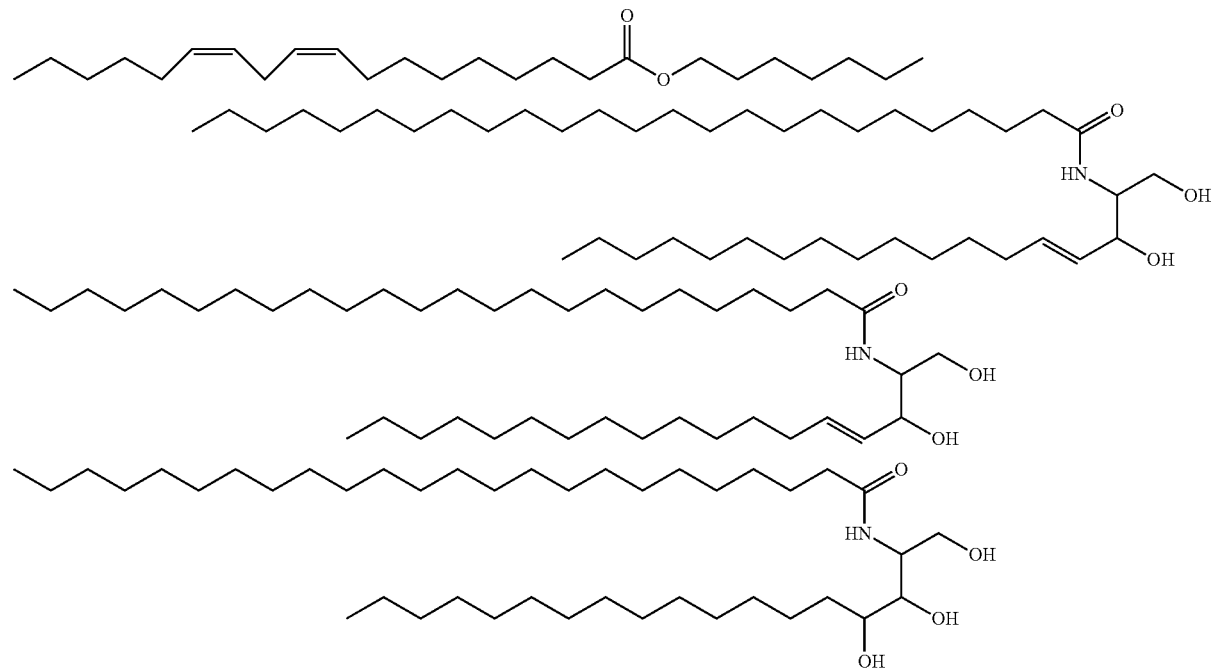

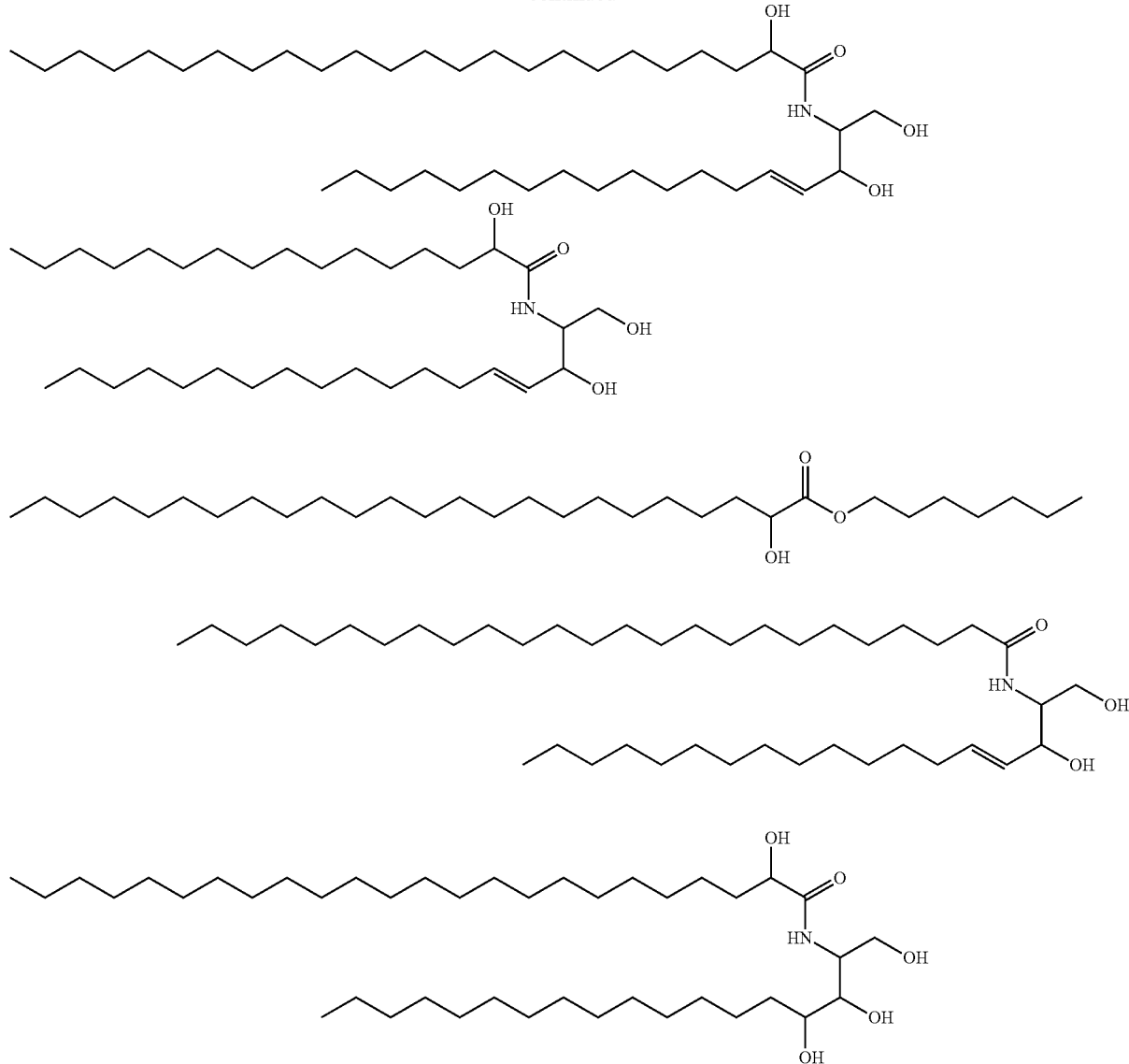

These may be an extract of a natural substance, or a synthetic product, and a commercially available product may also be used. Examples of commercially available ceramides include Ceramide I, Ceramide III, Ceramide IIIA, Ceramide IIIB, Ceramide IIIC, Ceramide VI (manufactured by Cosmoferm), Ceramide TIC-001 (manufactured by Takasago International Corporation), CERAMIDE II (manufactured by Quest International), DS-Ceramide VI, DS-CLA-Phytoceramide, Phytoceramide, DS-ceramide Y3S (manufactured by DOOSAN) and CERAMIDE 2 (manufactured by Sederma).

Ceramide III

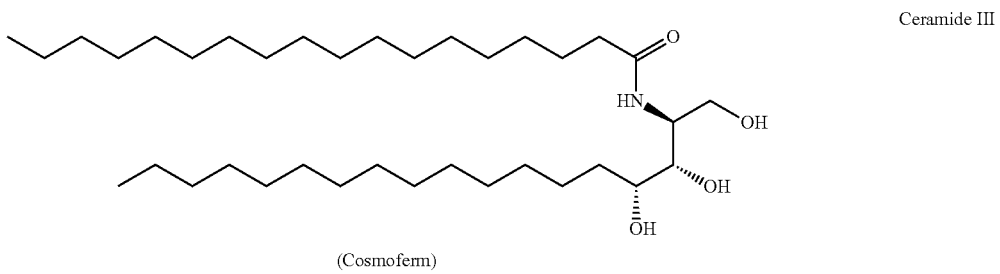

(Cosmoferm)

-continued
Ceramide IIIB
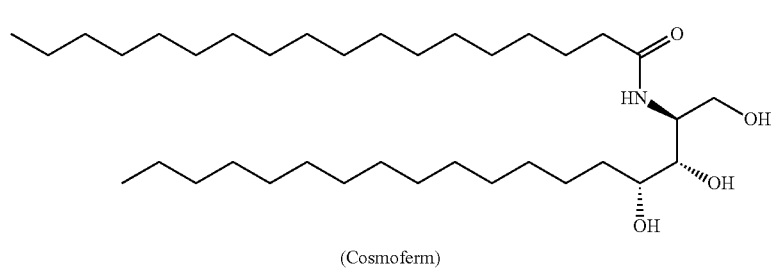
(Cosmoferm)
Ceramide IIIA
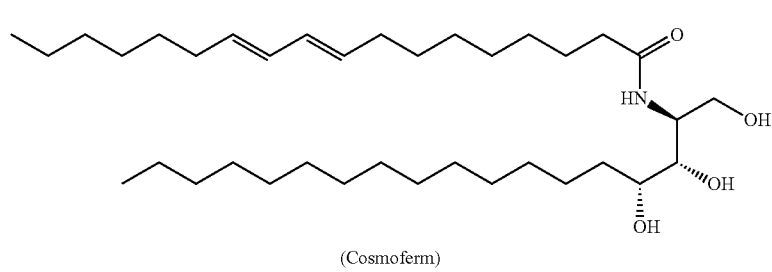
(Cosmoferm)
Phytoceramide
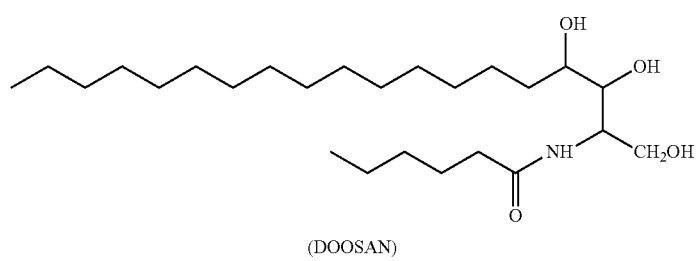
(DOOSAN)
DS-CLA-Phytoceramide
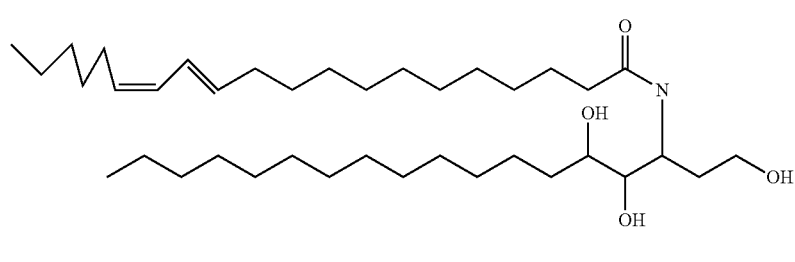
(DOOSAN)
DS-Ceramide VI
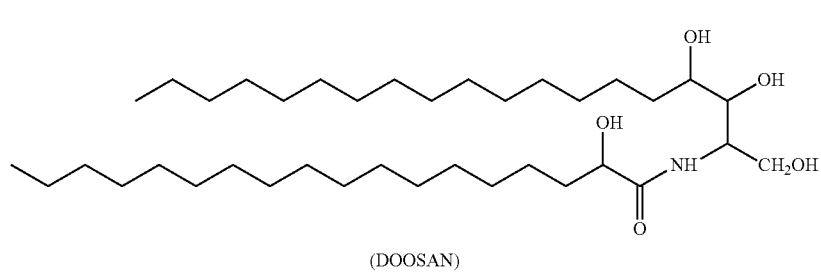
(DOOSAN)
Ceramide IV
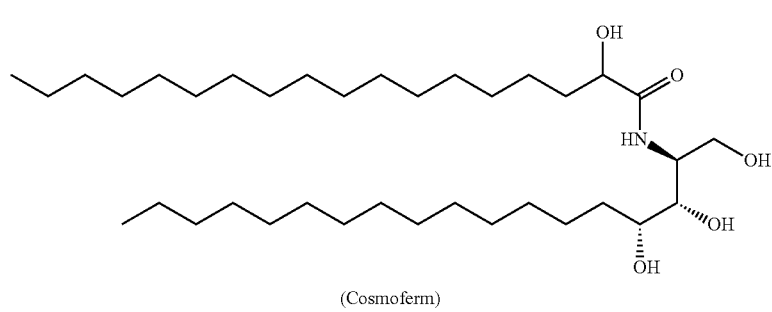
(Cosmoferm)

-continued

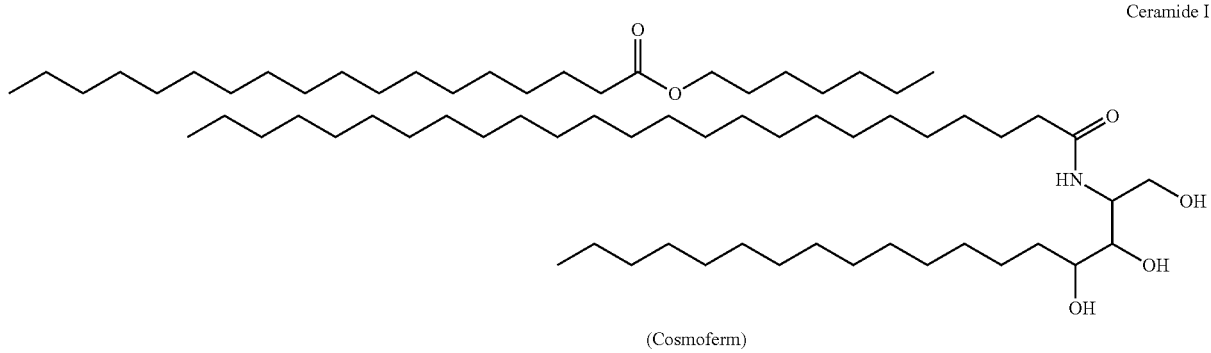

Ceramide I (Cosmoferm)

Furthermore, examples of pseudo-ceramides include those represented by the following formula (5):

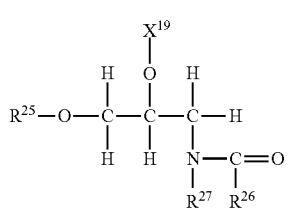

(5)

wherein $R^{25}$ represents a linear, branched or cyclic, saturated or unsaturated hydrocarbon group having 10 to 22 carbon atoms and optionally substituted by a hydroxyl group, or a hydrogen atom; $X^{19}$ represents a hydrogen atom, an acetyl group or a glyceryl group; $R^{26}$ represents a linear, branched or cyclic, saturated or unsaturated hydrocarbon group having 5 to 22 carbon atoms and optionally substituted by a hydroxyl group or amino group, or the above hydrocarbon group to which a linear or branched, saturated or unsaturated fatty acid having 8 to 22 carbon atoms and optionally substituted by a hydroxyl group is ester-bonded at the ω terminal; and $R^{27}$ represents a hydrogen atom, or an alkyl group having a total of 1 to 30 carbon atoms and optionally substituted by a hydroxyl group, hydroxyalkoxy group, alkoxy group or acetoxy group.

$R^{26}$ is particularly preferably a nonyl group, a tridecyl group, a pentadecyl group, an undecyl group to which linoleic acid is ester-bonded at the ω position, a pentadecyl group to which linoleic acid is ester-bonded at the ω position, a pentadecyl group to which 12-hydroxystearic acid is ester-bonded at the ω position, and an undecyl group to which methyl branched isostearic acid is amide-bonded at the ω position.

It is preferable that when $R^{25}$ is a hydrogen atom, $R^{27}$ is an alkyl group having a total of 10 to 30, preferably 12 to 20 carbon atoms and optionally substituted by a hydroxyl group, hydroxyalkoxy group, alkoxy group or acetoxy group; when $R^{25}$ is a linear, branched or cyclic, saturated or unsaturated hydrocarbon group having 10 to 22 carbon atoms and optionally substituted by a hydroxyl group, $R^{27}$ represents a hydrogen atom, or an alkyl group having a total of 1 to 8 carbon atoms and optionally substituted by a hydroxyl group, hydroxyalkoxy group, alkoxy group or acetoxy group. The hydroxyalkoxy group or alkoxy group of $R^{27}$ is preferably those having 1 to 7 carbon atoms.

Specific examples of compounds represented by the above formula (5) include compounds represented by the following formula.

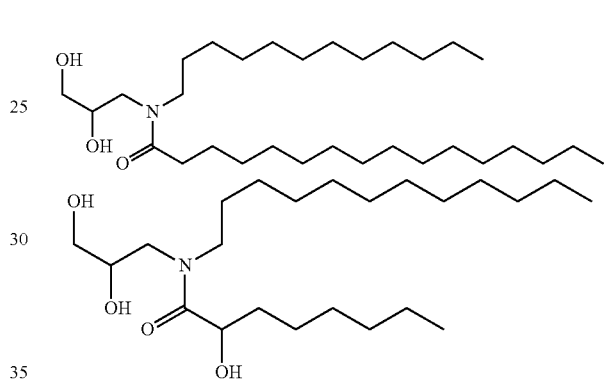

The compound represented by the formula (5) is preferably a pseudo-ceramide in which $R^{25}$ is a hexadecyl group, $X^{19}$ is a hydrogen atom, $R^{26}$ is a pentadecyl group and $R^{27}$ is a hydroxyethyl group; or in which $R^{25}$ is a hexadecyl group, $X^{19}$ is a hydrogen atom, $R^{26}$ is a nonyl group and $R^{27}$ is a hydroxyethyl group. The compound of the formula (5) is further preferably one in which $R^{25}$ is a hexadecyl group, $X^{19}$ is a hydrogen atom, $R^{26}$ is a pentadecyl group and $R^{27}$ is a hydroxyethyl group (N-(hexadecyloxyhydroxypropyl)-N-hydroxyethylhexadecanamide). Those represented by the following formula are also preferred.

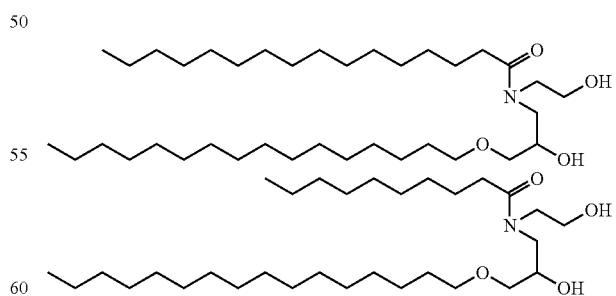

In the present embodiment, the content of the component (C) in the emulsion composition is preferably from 0.05 to 15% by mass, more preferably from 0.1 to 13% by mass, further preferably from 0.5 to 10% by mass, and yet more preferably from 0.8 to 5% by mass based on the whole emulsion composition to improve emulsification stability of the emulsion composition and reduce stickiness when applied.

Furthermore, for the components (A), (B) and (C), the mass ratio of the amount of the component (C) to the total amount of the components (A), (B) and (C), i.e., the mass ratio represented by ((C)/((A)+(B)+(C))) is preferably 0.4 or more, more preferably 0.45 or more, further preferably 0.5 or more, still more preferably 0.52 or more, and particularly preferably 0.55 or more to improve emulsification stability of the emulsion composition at low temperature and feeling on use. The mass ratio represented by ((C)/((A)+(B)+(C))) is preferably less than 1.0, more preferably 0.95 or less, further preferably 0.9 or less, still more preferably 0.85 or less, and yet more preferably 0.8 or less in order to suppress precipitation of the component (C) when stored at low temperature.

The mass ratio represented by ((C)/((A)+(B))) is preferably from 0.5 to 3.5, more preferably from 0.7 to 3.0, and further preferably from 1.0 to 2.8 to improve emulsification stability of the emulsion composition at low temperature and feeling on use and to suppress precipitation of the component (C) when stored at low temperature.

(Component (D))

The component (D) is one or more selected from the group consisting of sphingosine, a salt thereof and an ionic surfactant.

For the component (D), examples of sphingosines and salts thereof include sphingosines represented by the following formula (1):

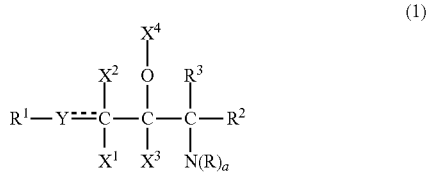

(1)

wherein $R^1$ is a linear, branched or cyclic, saturated or unsaturated hydrocarbon group having 4 to 30 carbon atoms and optionally substituted by a hydroxyl group, carbonyl group or amino group; Y is a methylene group, a methine group or an oxygen atom; $X^1$, $X^2$ and $X^3$ each independently represent a hydrogen atom, a hydroxyl group or an acetoxy group, $X^4$ represents a hydrogen atom, an acetyl group or a glyceryl group, or forms an oxo group together with an adjacent oxygen atom (provided that when Y is a methine group, one of $X^1$ and $X^2$ is a hydrogen atom, and the other is not present; when $X^4$ forms an oxo group, $X^3$ is not present); $R^2$ and $R^3$ each independently represent a hydrogen atom, a hydroxyl group, a hydroxymethyl group or an acetoxymethyl group; a Rs each independently represent a hydrogen atom or an amidino group, or a linear or branched, saturated or unsaturated hydrocarbon group having a total of 1 to 8 carbon atoms and optionally having a substituent selected from a hydroxyl group, a hydroxyalkoxy group, an alkoxy group and an acetoxy group; a represents a number of 2 or 3; and the dotted line represents an optional unsaturated bond.

In the formula, $R^1$ is a linear, branched or cyclic, saturated or unsaturated hydrocarbon group having 4 to 30 carbon atoms and optionally substituted by a hydroxyl group, carbonyl group or amino group, and preferably a linear, branched or cyclic, saturated or unsaturated hydrocarbon group having 7 to 22 carbon atoms and optionally substituted by a hydroxyl group. In particular, for example, a linear or branched alkyl group having 10 to 20 carbon atoms, and a linear or branched alkyl group having 10 to 20 carbon atoms and having a hydroxyl group at the terminal Y are preferred, and in the case of a branched alkyl group, one having a methyl branch is preferred. Specifically, a tridecyl group, a tetradecyl group, pentadecyl group, hexadecyl group, 1-hydroxytridecyl group, 1-hydroxypentadecyl group, an isohexadecyl group and an isostearyl group are preferred.

Y represents any of a methylene group ($CH_2$), a methine group (CH) or an oxygen atom.

$X^1$, $X^2$ and $X^3$ each independently represent a hydrogen atom, a hydroxyl group or an acetoxy group, and $X^4$ represents a hydrogen atom, an acetyl group or a glyceryl group, or a substituent forming an oxo group together with an adjacent oxygen atom. In particular, one in which 0 or 1 of $X^1$, $X^2$ and $X^3$ is a hydroxyl group, the rest is a hydrogen atom, and $X^4$ is a hydrogen atom is preferred. When Y is a methine group, one of $X^1$ and $X^2$ is a hydrogen atom, and the other is not present. When $X^4$ forms an oxo group, $X^3$ is not present.

$R^2$ and $R^3$ each dependently represent a hydrogen atom, a hydroxyl group, a hydroxymethyl group or an acetoxymethyl group, and $R^3$ is more preferably a hydrogen atom.

Furthermore, a represents a number of 2 or 3, and when a is 2, R represents $R^4$ and $R^5$, and when a is 3, R represents $R^4$, $R^5$ and $R^6$.

$R^4$, $R^5$ and $R^6$ each independently represent a hydrogen atom, an amidino group, or a linear or branched, saturated or unsaturated hydrocarbon group having a total of 1 to 8 carbon atoms, and optionally having a substituent selected from a hydroxyl group, a hydroxyalkoxy group, an alkoxy group and an acetoxy group. The hydroxyalkoxy group by which the hydrocarbon group is optionally substituted is preferably a linear or branched hydroxyalkoxy group having 1 to 7 carbon atoms. Furthermore, a linear or branched alkoxy group having 1 to 7 carbon atoms is preferred as the alkoxy group. Examples of $R^4$, $R^5$ and $R^6$ include a hydrogen atom; a linear or branched alkyl group such as methyl, ethyl, propyl, 2-ethylhexyl and isopropyl; an alkenyl group such as vinyl and allyl; an amidino group; a hydrocarbon group having a total of 1 to 8 carbon atoms, which is substituted by 1 to 6 selected from a hydroxyl group, a hydroxyalkoxy group and an alkoxy group, such as hydroxymethyl, 2-hydroxyethyl, 1,1-dimethyl-2-hydroxyethyl, 2-hydroxypropyl, 2,3-dihydroxypropyl, 2-hydroxy-3-methoxypropyl, 2,3,4,5,6-pentahydroxyhexyl, 1,1-bis(hydroxymethyl)ethyl, 2-(2-hydroxyethoxy)ethyl, 2-methoxyethyl, 1-methyl-2-hydroxyethyl, 3-hydroxypropyl, 3-methoxypropyl and 1,1-bis(hydroxymethyl)-2-hydroxyethyl.

In particular, a hydrogen atom, a methyl group, and an alkyl group optionally substituted by 1 to 3 selected from a hydroxyl group and a hydroxyalkoxy group, such as 2-hydroxyethyl, 1,1-dimethyl-2-hydroxyethyl, 1,1-bis(hydroxymethyl)ethyl and 2-(2-hydroxyethoxy)ethyl, are preferred.

A naturally derived sphingosine represented by the following formula (2) and a synthesized product having the same structure are preferred as the sphingosine represented by the formula (1):

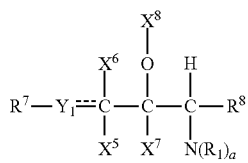

(2)

wherein R[7] is a linear, branched or cyclic, saturated or unsaturated hydrocarbon group having 7 to 19 carbon atoms and optionally substituted by a hydroxyl group; $Y_1$ is a methylene group or a methine group; $X^5$, $X^6$ and $X^7$ each independently represent a hydrogen atom, a hydroxyl group or an acetoxy group; $X^8$ represents a hydrogen atom or forms an oxo group together with an adjacent oxygen atom (provided that when $Y_1$ is a methine group, one of $X^5$ and $X^6$ is a hydrogen atom, and the other is not present; when $X^8$ forms an oxo group, $X^7$ is not present); $R^8$ represents a hydroxymethyl group or an acetoxymethyl group; a $R_1$s each independently represent a hydrogen atom or an amidino group or a linear or branched, saturated or unsaturated hydrocarbon group having a total of 1 to 4 carbon atoms and optionally having a substituent selected from a hydroxyl group, a hydroxyalkoxy group, an alkoxy group and an acetoxy group; a represents a number of 2 or 3; and the dotted line represents an optional unsaturated bond.

Here, $R^7$ is preferably a linear, branched or cyclic, saturated or unsaturated hydrocarbon group having 7 to 19 carbon atoms, and particularly preferably a linear saturated or unsaturated hydrocarbon group having 13 to 15 carbon atoms. a is preferably 2. $R_1$ is preferably each independently a hydrogen atom, or a linear or branched alkyl group having 1 to 4 carbon atoms.

Specifically, examples of the natural sphingosines represented by the formula (2) include natural sphingosine, dihydrosphingosine, phytosphingosine, sphingadienine, dehydrosphingosine, dehydrophytosphingosine, and an N-alkyl form (e.g., an N-methyl form) thereof.

For these sphingosines, natural optically active forms (D(+) forms), unnatural optically active forms (L(-) forms), and a mixture of a natural form and an unnatural form may be used. The relative configuration of the above forms may be ones of natural type or unnatural type other than those, or of mixed type.

In particular, PHYTOSPHINGOSINE (INCI name, 8th Edition) and those represented by the following formula are preferred.

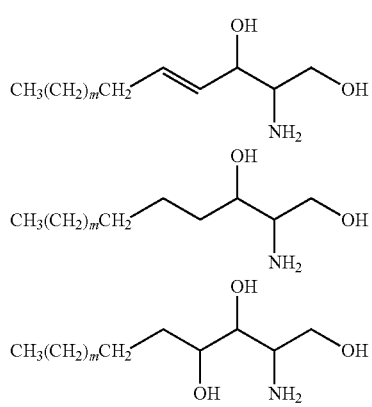

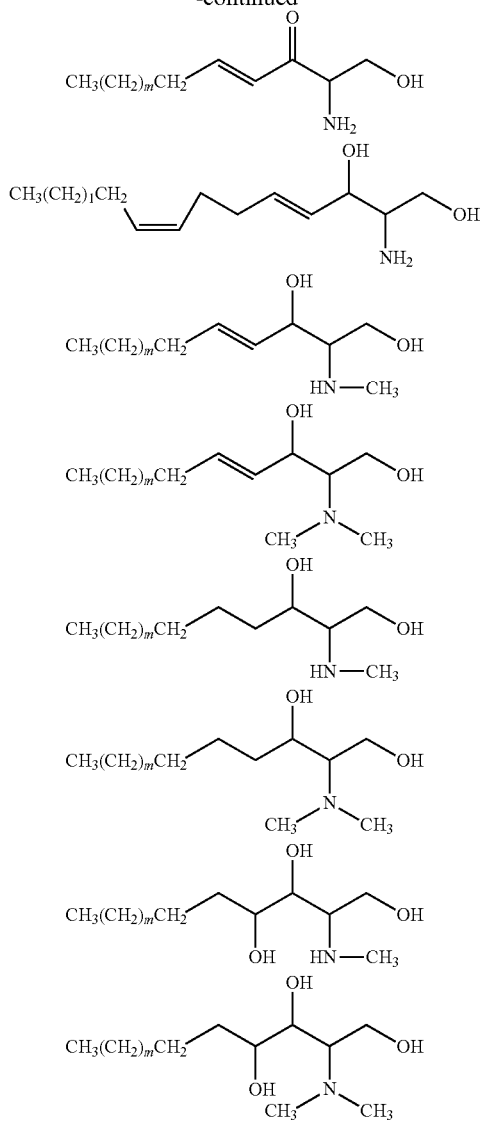

(in the formula m represents a number of 5 to 17 and l represents a number of 1 to 13.)

These may be an extract from a natural substance, or a synthetic product, and a commercially available product may also be used. Examples of commercially available sphingosines include D-Sphingosine (4-Sphingenine) (manufactured by SIGMA-ALDRICH), DS-phytosphingosine (manufactured by DOOSAN) and phytosphingosine (manufactured by Cosmoferm).

Examples of the salts of such sphingosines include a salt of acidic amino acids such as glutamic acid and aspartic acid; a salt of basic amino acids such as arginine; a salt of inorganic acids such as phosphoric acid and hydrochloric acid; a salt of monocarboxylic acid such as acetic acid; a salt of dicarboxylic acid such as succinic acid; and a salt of oxycarboxylic acid such as citric acid, lactic acid and malic acid. One or more selected therefrom are preferred.

Next, among the component (D), examples of ionic surfactants include an anionic surfactant, a cationic surfactant and an amphoteric surfactant.

Examples of anionic surfactants include fatty acids having 12 to 22 carbon atoms such as sodium laurate, potassium palmitate and arginine stearate, or a salt thereof; alkyl sulfate esters having 12 to 22 carbon atoms, such as sodium lauryl sulfate, potassium lauryl sulfate and sodium cetyl sulfate, or a salt thereof;

alkyl ether sulfate esters having 12 to 22 carbon atoms such as polyoxyethylene lauryl sulfate triethanolamine, or a salt thereof;

alkyl ether acetate esters having 12 to 22 carbon atoms such as sodium polyoxyethylene tridecylether acetate, or a salt thereof;

N-acyl sarcosines having 12 to 22 carbon atoms such as sodium lauroyl sarcosine, or a salt thereof;

alkyl phosphates having 12 to 22 carbon atoms such as sodium monostearyl phosphate, or a salt thereof;

polyoxyethylene alkyl ether phosphates having 12 to 22 carbon atoms such as sodium polyoxyethylene oleyl ether phosphate and sodium polyoxyethylene stearyl ether phosphate, or a salt thereof;

dialkyl sulfosuccinates having 12 to 24 carbon atoms such as sodium di-2-ethylhexyl sulfosuccinate, or a salt thereof;

N-alkyloyl methyl taurine having 12 to 22 carbon atoms such as sodium N-stearoyl-N-methyl taurine, or a salt thereof; and acyl glycine having 12 to 22 carbon atoms such as sodium N-coco acyl glycinate, or a salt thereof;

acyl alanine having 12 to 22 carbon atoms such as sodium N-coco acyl alaninate, or a salt thereof; or N-acyl glutamate having 12 to 22 carbon atoms such as sodium dilauroyl glutamate, monosodium N-lauroyl glutamate, sodium N-stearoyl-L-glutamate, arginine N-stearoyl-L-glutamate, sodium N-stearoyl glutamate and sodium N-myristoyl-L-glutamate, or a salt thereof, acylaspartate, diacyl glutamic acid lysine salt, acyl arginine salt, dialkyldimethylammonium salt and alkyltrimethylammonium salt.

Examples of the cationic surfactants include a quaternary ammonium salt and an amine salt. Quaternary ammonium salts are preferred in order to improve emulsification stability of the emulsion composition, and examples thereof include alkyl trimethyl ammonium salts such as stearyl trimethyl ammonium chloride and behenyl trimethyl ammonium chloride, dialkyl dimethyl ammonium salt and trialkyl methyl ammonium salt.

Furthermore, examples of amphoteric surfactants include alkyl dimethyl amine oxide, alkyl carboxyl betaine, alkyl sulfobetaine, amido amino acid salt and alkyl amido propyl betaine. Alkyl amido propyl betaine is particularly preferred.

One or more selected from the group consisting of sphingosine, a salt thereof and an anionic surfactant is preferred as the component (D) in order to improve emulsification stability of the emulsion composition.

Furthermore, a compound other than fatty acid or a salt thereof is preferred as the anionic surfactant in order to improve emulsification stability of the emulsion composition. One or more selected from the group consisting of polyoxyethylene alkyl ether phosphate having 12 to 22 carbon atoms, N-alkyloyl methyl taurate having 12 to 22 carbon atoms and N-acylglutamate having 12 to 22 carbon atoms are preferred. One or two selected from the group consisting of N-acylglutamate having 12 to 22 carbon atoms or a salt thereof, and N-alkyloyl methyl taurate having 12 to 22 carbon atoms are more preferred in order to obtain excellent feeling on use. N-stearoyl-L-glutamate is preferred as N-acylglutamate having 12 to 22 carbon atoms in order to improve emulsification stability of the emulsion composition and obtain excellent feeling on use. Arginine N-stearoyl-L-glutamate and potassium N-stearoyl-L-glutamate are more preferred. N-alkyloyl methyl taurate having 12 to 22 carbon atoms is preferred, N-alkyloyl methyl taurate having 14 to 20 carbon atoms is more preferred, and N-alkyloyl methyl taurate having 16 to 20 carbon atoms is further preferred in order to improve emulsification stability of the emulsion composition and obtain excellent feeling on use.

Furthermore, it is preferable that the component (D) contains one or more selected from the group consisting of phytosphingosine or a salt thereof, pseudo-sphingosine salt, acylglutamate, acylaspartate, acyl methyl taurate, fatty acid salt, diacyl glutamic acid lysine salt, acyl arginine salt, dialkyldimethylammonium salt and alkyltrimethylammonium salt in order to suppress precipitation of the component (C) and improve emulsification stability of the emulsion composition. Phytosphingosine or a salt thereof and acyl methyl taurate are more preferred, and acyl methyl taurate is further preferred in order to obtain excellent feeling on use, in particular, good spreadability.

The component (D) may be used singly or in combination of two or more.

The content of the component (D) represents the content of the compound excluding counter ions. The content is, for example, from 0.01 to 10% by mass, preferably from 0.05 to 5% by mass, more preferably from 0.1 to 3% by mass, further preferably from 0.1 to 2% by mass, and particularly preferably from 0.3 to 1% by mass based on the whole emulsion composition in order to disperse the respective components described later in a stable manner and obtain non-sticky feeling on use and to suppress friction feeling when applied.

For the components (A), (B), (C) and (D), the mass ratio of the amount of the component (D) to the total amount of the components (A), (B) and (C), i.e., the mass ratio represented by ((D)/((A)+(B)+(C))) is preferably more than 0, and more preferably 0.03 or more, further preferably 0.08 or more, and still more preferably 0.10 or more in order to improve emulsification stability of the emulsion composition at low temperature, to suppress precipitation of the component (C) when stored at low temperature, and to improve feeling on use. Furthermore, the mass ratio represented by ((D)/((A)+(B)+(C))) is preferably 0.5 or less, more preferably 0.4 or less, further preferably 0.35 or less, still more preferably 0.30 or less, yet more preferably 0.2 or less, and particularly preferably 0.15 or less in order to improve the balance between emulsification stability of the emulsion composition at low temperature and feeling on use.

Furthermore, in the emulsion composition of the present embodiment, the total content of the components (A) to (D), i.e., the mass ratio represented by ((A)+(B)+(C)+(D)), is preferably from 0.3 to 15% by mass, more preferably from 0.5 to 12% by mass, further preferably from 1 to 10% by mass, still more preferably from 2 to 8% by mass, especially preferably from 3.5 to 7% by mass, and particularly preferably from 3.5 to 5% by mass based on the whole emulsion composition to improve emulsification stability of the emulsion composition.

The emulsion composition of the present embodiment is a W/O emulsion composition containing the above components (A) to (D). It is preferable that in order to improve emulsification stability of the emulsion composition and to obtain excellent feeling on use, the aqueous phase of the W/O emulsion composition contains the components (A) to (D). An O1/W/O emulsion composition in which an inner oil phase O1 is dispersed in the aqueous phase of the W/O emulsion composition is more preferred.

More specifically, the inner oil phase in the emulsion composition of the present embodiment has a lamellar α-gel structure. The emulsion composition in the present embodiment imparts excellent feeling on use, in particular, lastingness of moist feeling. This is assumed that because solid lipid in the emulsion composition forms a lamellar coating of an α-gel structure on the surface of the skin, and due to the synergistic effect with the outer oil phase, the oil agent stays on the surface of the skin for a long time as a lamellar coating.

Thus, it is preferable that in the present embodiment, the inner oil phase O1 contains the components (A) to (D) in order to obtain a cosmetic in which crystallization of a ceramide is suppressed when stored at low temperature and a ceramide is compounded in a stable manner and which provides excellent feeling on use.

(Component (E))

The component (E) is a nonionic surfactant containing the following (e1) and (e2).

(e1) one or more selected from the group consisting of a crosslinked polyether-modified silicone and a crosslinked polyglycerol-modified silicone (e2) one or more selected from the group consisting of a polyether-modified silicone, a polyglycerol-modified silicone and a polyglycerol fatty acid ester.

A combination use of (e1) and (e2) improves storage stability under temperature cycle conditions and feeling on use (thickness) of cosmetic.

The crosslinked polyether-modified silicone (e1) is a ternary crosslinked product in which organopolysiloxane chains are crosslinked by polyether. Examples thereof include a crosslinked polyether-modified silicone represented by the following formula (3):

is a number of from 10 to 200, j is a number of from 1 to 50 and k is a number of from 1 to 50.

The crosslinked polyether-modified silicone (e1) may be produced by the method described in JP-A-1992-272932.

Furthermore, the crosslinked polyether-modified silicone (e1) is preferably diluted or dispersed in a volatile hydrocarbon oil or a silicone oil. The volatile hydrocarbon oil is more preferably isododecane and polyisobutene.

A commercially available product such as KSG-210, KSG-240 (dimethicone/(PEG-10/15)) crosspolymer); KSG-310, KSG-320, KSG-330 ((PEG-15/lauryl dimethicone) crosspolymer); KSG-340 ((PEG-10/lauryl dimethicone) crosspolymer and (PEG-15/lauryl dimethicone) crosspolymer) (manufactured by Shin-Etsu Chemical Co., Ltd.) may be used as the crosslinked polyether-modified silicone (e1).

One or more of the crosslinked polyether-modified silicones may be used.

The crosslinked polyglycerol-modified silicone (e1) is a three-dimensional crosslinked product in which organopolysiloxane chains are crosslinked by polycerol. Specific examples thereof include (dimethicone/polyglycerol-3) crosspolymer and alkyl co-modified (lauryl dimethicone/polyglycerol-3) crosspolymer, and a commercially available product such as KSG-710 (dimethicone/polyglycerol-3) crosspolymer), KSG-810 (lauryl dimethicone/polyglycerol-3) crosspolymer)(manufactured by Shin-Etsu Chemical Co., Ltd.) may be used.

One or more of the crosslinked polyglycerol-modified silicones may be used.

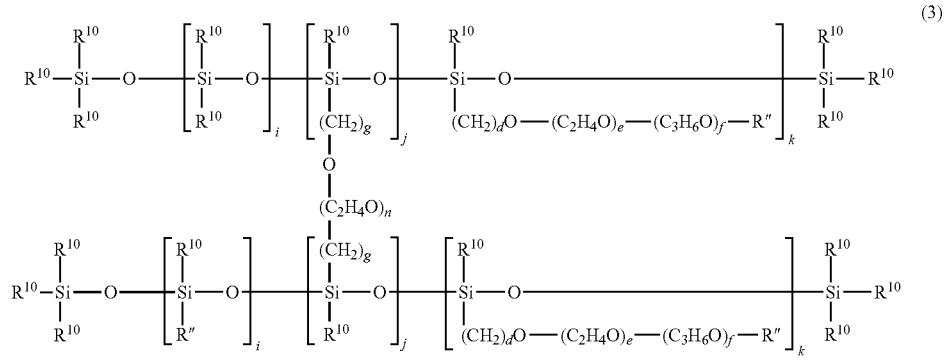

wherein $R^{10}$ represents a methyl group or a phenyl group, each R' represents a hydrogen atom, an alkyl group or an acyl group having 1 to 30 carbon atoms, each R" represents an alkyl group or an acyl group having 1 to 30 carbon atoms, or a siloxane group having 1 to 30 silicon atoms; d represents a number of from 1 to 20, e and f represent a number of from 0 to 200, and e and f are not simultaneously 0; g is a number of from 0 to 30, h represents a number of from 1 to 100, i represents a number of from 10 to 2,000, j represents a number of from 1 to 1,000, and k represents a number of from 1 to 1,000.

In the formula (1), R" is preferably an alkyl group having 1 to 15 carbon atoms. Furthermore, it is preferable that g is a number of from 0 to 15, h is a number of from 1 to 40, i The content of the component (e1) is preferably 0.1% by mass or more and 10% by mass or less, more preferably 0.2% by mass or more and 5% by mass or less, further preferably 0.5% by mass or more and 2% by mass or less based on the whole emulsion composition in consideration of storage stability under temperature cycle conditions and feeling on use.

It is more preferable to use a crosslinked polyether-modified silicone as the component (e1) in consideration of storage stability under temperature cycle conditions and feeling on use.

The polyether-modified silicone of the component (e2) refers to silicone having a monovalent polyoxyalkyl group in the structure, and examples thereof include a compound represented by the formula (4):

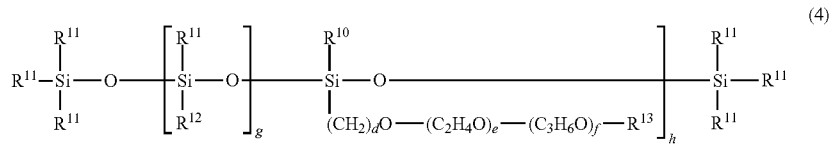

(4)

wherein each $R^{11}$ is the same or different and represents a methyl group or a phenyl group, $R^{13}$ represents a hydrogen atom, an alkyl group or an acyl group having 1 to 30 carbon atoms, $R^{12}$ is an alkyl group or an acyl group having 1 to 30 carbon atoms, or a siloxane group having 1 to 30 silicon atoms, d is a number of from 1 to 20, e and f are a number of from 0 to 200, e and f are not simultaneously 0; g is a number of from 10 to 2,000, h represents a number of from 1 to 1000.

Preferably, in the formula (4), d is a number of from 1 to 10, e is a number of from 1 to 50, f is a number of from 1 to 50, g is a number of from 10 to 1,000 and h is a number of from 1 to 50.

Examples of polyether-modified silicones of the component (e2) include PEG-3 dimethicone, PEG-10 dimethicone, PEG-12 dimethicone, PEG-11 methyl ether dimethicone, PEG-9 polydimethylsiloxyethyl dimethicone and cetyl PEG/PPG-10/1 dimethicone. Examples of commercially available products include KF-6011, KF-6015, KF-6017, KF-6025, KF-6028, and KF-6048 (manufactured by Shin-Etsu Chemical Co., Ltd.).

The polyglycerol-modified silicone of the component (e2) refers to silicone having a monovalent polyglycerol group in the structure, and examples thereof include polyglycerol-3 disiloxane dimethicone and polyglycerol-3 polydimethylsiloxyethyl dimethicone. Examples of commercially available products include KF-6100, and KF-6104 (manufactured by Shin-Etsu Chemical Co., Ltd.).

One or more of the components (e2) may be used.

Examples of polyglycerol fatty acid esters of the component (e2) include diglycerol fatty acid esters and triglycerol fatty acid esters. Diglycerol fatty acid esters are preferred in order to improve storage stability under temperature cycle conditions. Furthermore, polyglycerol fatty acid esters derived from fatty acid having preferably 12 to 22, more preferably 14 to 20 carbon atoms are preferred, and polyglycerol fatty acid esters derived from saturated fatty acid are more preferred, from the same point of view.

Using polyether-modified silicone and/or polyglycerol fatty acid ester as the component (e2) is more preferred in consideration of storage stability under temperature cycle conditions and feeling on use.

One or more of the components (e2) may be used.

The content of the component (e2) is preferably 0.1% by mass or more and 10% by mass or less, more preferably 1% by mass or more and 7% by mass or less, further preferably 1.5% by mass or more and 5% by mass or less, and yet more preferably 1.5% by mass or more and 4% by mass or less based on the whole emulsion composition in consideration of storage stability under temperature cycle conditions and feeling on use.

In the present invention, both of the component (e1) and the component (e2) are used together as the nonionic surfactant (E). The mass ratio of the content of the component (e1) and the content of the component (e2), (e2/e1), is preferably 0.1 or more and 10 or less, more preferably 0.1 or more and 8 or less, further preferably 1 or more and 7 or less, and still more preferably 3 or more and 5 or less in consideration of storage stability under temperature cycle conditions and feeling on use.

Meanwhile, the surface of the skin is kept slightly acidic in order to maintain homeostasis. Thus, to design a low irritant external agent for the skin, it is required that the formulation has a slightly acidic pH close to the pH of the skin. Furthermore, using an anionic surfactant as the ionic surfactant in an external agent for the skin is more preferred considering application to users of all ages and all skin types. However, when an anionic surfactant is used for stable emulsification and dispersion of a ceramide, slightly acidic pH reduces the surface activity of the surfactant, and there is a problem in the emulsification stability at high temperature storage.

Thus, when the W/O emulsion composition of the present invention contains an anionic surfactant as the component (D) and also (F) a nonionic surfactant other than (e1) or (e2), having an HLB of 8 or more and (G) one or more selected from the group consisting of an inorganic acid and an organic acid having 6 or less carbon atoms, change in the viscosity of the composition is small even after being stored at high temperature of 50° C. or more, the emulsified system has excellent stability, and the composition has excellent feeling on use such as lasting moist feeling, thickness, feeling of moisturizing the skin, and making the skin smooth without friction when applied.

the anionic surfactant as described above is preferred as the anionic surfactant (D) used in the present embodiment. That is, examples of anionic surfactants of the component (D) in the present embodiment include fatty acids having 12 to 22 carbon atoms such as sodium laurate, potassium palmitate and arginine stearate, or a salt thereof;

alkyl sulfate esters having 12 to 22 carbon atoms such as sodium lauryl sulfate, potassium lauryl sulfate and sodium cetyl sulfate, or a salt thereof;

alkyl ether sulfate esters having 12 to 22 carbon atoms such as polyoxyethylene lauryl sulfate triethanolamine, or a salt thereof;

alkyl ether acetate esters having 12 to 22 carbon atoms such as sodium polyoxyethylene tridecylether acetate, or a salt thereof N-acyl sarcosines having 12 to 22 carbon atoms such as sodium lauroyl sarcosine, or a salt thereof;

alkyl phosphates having 12 to 22 carbon atoms such as sodium monostearyl phosphate, or a salt thereof;

alkyl ether phosphate having 12 to 22 carbon atoms such as sodium polyoxyethylene oleyl ether phosphate and sodium polyoxyethylene stearyl ether phosphate, or a salt thereof;

dialkyl sulfosuccinate having 12 to 24 carbon atoms such as sodium di-2-ethylhexyl sulfosuccinate, or a salt thereof;

N-alkyloyl methyl taurine having 12 to 22 carbon atoms such as sodium N-stearoyl-N-methyl taurine, or a salt thereof;

acyl glycine having 12 to 22 carbon atoms such as sodium N-coco acyl glycinate, or a salt thereof;

acyl alanine having 12 to 22 carbon atoms such as sodium N-coco acyl alaninate, or a salt thereof; and N-acyl glutamate having 12 to 22 carbon atoms such as sodium dilauroyl glutamate, monosodium N-lauroyl glutamate, sodium N-stearoyl-L-glutamate, arginine N-stearoyl-L-glutamate, sodium N-stearoyl glutamate and sodium N-myristoyl-L-glutamate, or a salt thereof.

Furthermore, a compound other than a fatty acid or a salt thereof is preferred as the component (D) in order to improve emulsification stability of the emulsion composition. One or more selected from the group consisting of polyoxyethylene alkyl ether phosphate having 12 to 22 carbon atoms or a salt thereof, N-alkyloyl methyl taurate having 12 to 22 carbon atoms and N-acylglutamate having 12 to 22 carbon atoms are preferred. One or two selected from the group consisting of N-acylglutamate having 12 to 22 carbon atoms or a salt thereof, and N-alkyloyl methyl taurate having 12 to 22 carbon atoms are more preferred in order to obtain excellent feeling on use. N-stearoyl-L-glutamate is preferred as N-acylglutamate having 12 to 22 carbon atoms in order to improve emulsification stability of the emulsion composition and obtain excellent feeling on use. Arginine N-stearoyl-L-glutamate and potassium N-stearoyl-L-glutamate are more preferred. As N-alkyloyl methyl taurate having 12 to 22 carbon atoms, N-alkyloyl methyl taurate having 12 to 22 carbon atoms is preferred, N-alkyloyl methyl taurate having 14 to 20 carbon atoms is more preferred, and N-alkyloyl methyl taurate having 16 to 20 carbon atoms is further preferred in order to improve emulsification stability of the emulsion composition and obtain excellent feeling on use.

Furthermore, it is preferable that the component (D) contains one or more selected from the group consisting of acyl methyl taurate, acylglutamate, acylaspartate, fatty acid salt, diacyl glutamic acid lysine salt and acyl arginine salt in order to suppress precipitation of the component (C) and improve emulsification stability of the emulsion composition.

The component (D) may also be used singly or in combination of two or more in the present embodiment.

The content of the component (D) is, for example, from 0.01 to 10% by mass, preferably from 0.05 to 5% by mass, more preferably from 0.1 to 3% by mass, further preferably from 0.3 to 2% by mass, and particularly preferably from 0.4 to 1% by mass based on the whole emulsion composition to disperse the respective components described later in a stable manner and obtain non-sticky feeling on use and suppress friction feeling when applied.

In the present embodiment, for the components (A), (B), (C) and (D), the mass ratio of the amount of the component (D) to the total amount of the components (A), (B) and (C), i.e., the mass ratio represented by ((D)/((A)+(B)+(C))) is preferably more than 0, and more preferably 0.03 or more, further preferably 0.08 or more, and still more preferably 0.10 or more in order to improve emulsification stability of the emulsion composition at low temperature, suppress precipitation of the component (C) when stored at low temperature, and improve feeling on use. Furthermore, the mass ratio represented by ((D)/((A)+(B)+(C))) is preferably 0.5 or less, more preferably 0.4 or less, further preferably 0.35 or less, yet more preferably 0.30 or less, and particularly preferably 0.2 or less in order to improve the balance between emulsification stability of the emulsion composition at low temperature and feeling on use.

Furthermore, in the emulsion composition of the present embodiment, the total content of the components (A) to (D), i.e., the mass ratio represented by ((A)+(B)+(C)+(D)), is preferably from 0.3 to 15% by mass, more preferably from 0.5 to 12% by mass, further preferably from 1 to 10% by mass, still more preferably from 2 to 8% by mass, especially preferably from 3.0 to 7% by mass, and particularly from 3.5 to 5% by mass based on the whole emulsion composition to improve emulsification stability of the emulsion composition.

The component (E) and its content in the present embodiment are the same as described above.

(Component (F))

The component (F) is a nonionic surfactant other than (e1) or (e2) mentioned above, having an HLB of 8 or more. In the present embodiment, using a nonionic surfactant having an HLB of 8 or more improves emulsification stability of a composition with an acidic compound in the aqueous phase under high temperature conditions, and feeling on use is not impaired due to separation, increased viscosity or gelation.

The nonionic surfactant has an HLB of preferably 8 or more and 20 or less, more preferably 10 or more and 20 or less, further preferably 10.7 or more and 20 or less, still more preferably 13 or more and 20 or less, and particularly preferably 14 or more and 20 or less in order to improve emulsification stability at high temperature, viscosity stability at high temperature and to obtain excellent feeling on use.

In this regard, HLB (hydrophilic-lipophilic balance) can be calculated by, for example, the following formula.

Formula: $[HLB]=7+1.171 \log(Mw/Mo)$ wherein Mw represents the molecular weight of the hydrophilic group of a surfactant, Mo represents the molecular weight of the hydrophobic group of the surfactant, and log represents a logarithm to base 10.

The nonionic surfactant having an HLB of 8 or more (F) is preferably one or more selected from polyoxyethylene hydrogenated castor oil, polyoxyethylene alkyl ether, polyoxyethylene sorbitan fatty acid ester, polyoxyethylene glycerol fatty acid ester, polyoxyethylene fatty acid ester, polypropylene glycol fatty acid ester, polyoxyethylene sorbitol fatty acid ester, polyglycerol fatty acid ester, polyoxyethylene polyoxypropylene alkyl ether, sucrose fatty acid ester and the like. Of them, one or more selected from the group consisting of polyoxyethylene hydrogenated castor oil, polyoxyethylene alkyl ether and polyoxyethylene fatty acid ester are more preferred in order to obtain emulsification stability at high temperature, viscosity stability at high temperature and excellent feeling on use.

In the present embodiment, one of the components (F) may be used, or two or more of them may be used in combination. In the present embodiment, the content of the component (F) is preferably from 0.05 to 1% by mass, more preferably from 0.1 to 1% by mass, further preferably from 0.15 to 0.8% by mass, and still more preferably from 0.2 to 0.7% by mass based on the whole emulsion composition in order to obtain emulsification stability at high temperature, viscosity stability at high temperature and excellent feeling on use.

The component (G) is an inorganic acid and an organic acid having 6 or less carbon atoms. When an inorganic acid and an organic acid is contained in the aqueous phase, feeling on use is improved while maintaining homeostasis of the surface of the skin.

Water-soluble organic acids are preferred as the organic acid and examples thereof include fatty acid having 1 to 6 carbon atoms, hydroxylic acid, dicarboxylic acid and acidic amino acid. Of them, one or more selected from the group consisting of malic acid, lactic acid, citric acid, succinic acid, acetic acid, tartaric acid, glutamic acid, aspartic acid and adipic acid are more preferred, and one or more selected from the group consisting of malic acid, lactic acid, citric acid, succinic acid, adipic acid and glutamic acid are further preferred, and succinic acid is particularly preferred in order to obtain excellent feeling on use.

One or more inorganic acids selected from the group consisting of hydrochloric acid, nitric acid, nitrous acid, sulfuric acid, sulfurous acid, phosphoric acid, phosphonic acid and phosphinic acid are preferred, and phosphoric acid is more preferred in order to obtain excellent feeling on use.

It is preferable that the pH of the aqueous phase is adjusted to be acidic by adding the component (G).

The pH of the aqueous phase is preferably from 3.0 to 7.0, and more preferably from 4.0 to 6.5

In the present embodiment, one of the components (G) may be used, or two or more of them may be used in combination. In the present embodiment, the content of the component (G) is preferably from 0.01 to 2% by mass, more preferably from 0.02 to 1% by mass, further preferably from 0.05 to 1% by mass, and still more preferably from 0.05 to 0.8% by mass, still more preferably from 0.05 to 0.5% by mass and particularly preferably from 0.1 to 0.2% by mass in order to improve feeling on use while maintaining emulsification stability at high temperature and homeostasis of the surface of the skin.

The mass ratio of the component (F) to the component (G), (F/G), is preferably 0.3 or more and 6.0 or less, more preferably 0.7 or more and 5.5 or less, and further preferably 1.0 or more and 5.0 or less, and still more preferably 1.2 or more and 4.0 or less in order to improve emulsification stability at high temperature and viscosity stability at high temperature, and to obtain excellent feeling on use, in particular, thickness and a smooth feeling of the skin when applied.

The mass ratio of the component (F) to the component (A), (F/A), is preferably 0.1 or more and 1.5 or less, more preferably 0.2 or more and 1.3 or less, further preferably 0.25 or more and 1.0 or less in order to improve emulsification stability at high temperature and viscosity stability at high temperature, and to obtain excellent feeling on use, in particular, thickness and a smooth touch of the skin when applied.

The emulsion composition of the present embodiment is a W/O emulsion composition containing the above components (A) to (G). It is preferable that in order to improve emulsification stability of the emulsion composition at low temperature and high temperature and viscosity stability at high temperature and to obtain excellent feeling on use, the aqueous phase of the W/O emulsion composition contains the components (A) to (D), (F) and (G). An O1/W/O emulsion cosmetic in which an inner oil phase O1 is dispersed in the aqueous phase of the W/O emulsion composition is more preferred.

More specifically, the inner oil phase in the emulsion composition of the present embodiment has a lamellar α-gel structure. The external agent for the skin in the present embodiment has excellent feeling on use, in particular, lastingness of moist feeling. This is considered because solid lipid in the emulsion composition forms a lamellar coating of an α-gel structure on the surface of the skin, and due to the synergistic effect with the outer oil phase, the oil agent stays on the surface of the skin for a long time as a lamellar coating.

Thus, it is preferable that in the present embodiment, the inner oil phase O1 contains the components (A) to (D) and (F) in order to obtain a cosmetic in which crystallization of a ceramide is suppressed when stored at low temperature and a ceramide is compounded in a stable manner and which provides excellent feeling on use.

The emulsion composition of the present invention may also contain, in addition to the above components, water, an oil component (H) other than the component (B), a thickener, a gel substance, amino acid, plant extract, a moisturizing agent, an anti-inflammatory agent, an antiseptic and the like.

Examples of the oil components (H) include those can be used in usual cosmetics, e.g., hydrocarbon oils such as liquid paraffin, squalan, vaseline and ceresin; ether oils such as cetyl dimethyl butyl ether (hereinafter also simply referred to as cetyl dimethyl butyl), ethylene glycol dioctyl ether and glycerol monooleyl ether; ester oils such as octyldodecyl myristate, isopropyl palmitate, butyl stearate, di-2-ethylhexyl adipate, neopentylglycol dicaprate, trioctanoin and isotridecyl isononanoate; silicone oils such as dimethyl polysiloxane, cyclic dimethyl polysiloxane, methylphenyl polysiloxane, amino-modified silicone, carboxy-modified silicone, alcohol-modified silicone, alkyl-modified silicone, polyether-modified silicone and fluorine-modified silicone; and fluorine oils such as perfluoroalkylethyl phosphoric acid, perfluoroalkyl polyoxyethylene phosphoric acid, perfluoropolyether and polytetrafluoroethylene. The raw material of ester oil and the like may be derived from a natural substance such as plant.

Of them, those containing liquid oil at 25° C. are preferred as the oil component (H) in the outer oil phase in order to improve feeling on use free from friction feeling. The liquid oil at 25° C. is preferably a hydrocarbon oil or a silicone oil, and more preferably both are included.

The mass ratio of hydrocarbon oil to silicone oil (hydrocarbon oil/silicone oil) is preferably from 15/1 to 1/1, more preferably from 8/1 to 1.5/1, and further preferably from 5/1 to 1/1 from the same point of view.

It is preferable that when these oil components are included, their content is from about 10 to 50% by mass based on the whole emulsion composition.

A polar oil having an IOB of 0.1 or more may also be used as the oil component (H) in the outer oil phase. The content is preferably 40% by mass or less, more preferably 20% by mass or less, and further preferably 1% by mass or less based on the entire outer oil phase O from the perspective of emulsification stability. It is most preferable that the composition does not contain a polar oil having an IOB of 0.1 or more.

Furthermore, examples of amino acids include neutral amino acids such as glycine, serine, cystine, alanine, threonine, cysteine, valine, phenylalanine, methionine, leucine, tyrosine, proline, isoleucine, tryptophan and hydroxyproline; acidic amino acids such as aspartic acid, asparagine, glutamine and glutamic acid; basic amino acids such as arginine, histidine and lysine; betaine, and amino acid derivatives such as acyl sarcosine and a salt thereof, acyl glutamic acid and a salt thereof, acyl-β-alanine and a salt thereof, glutathione, pyrrolidone carboxylic acid and a salt thereof, oligopeptide such as glutathione, carnosine, gramicidin S, tyrocidine A and tyrocidine B, and guanidine derivatives and a salt thereof described in JP-A-1994-228023.

It is preferable that when these amino acids are included, their content is from about 0.001 to 3% by mass based on the whole emulsion composition.

Examples of plant extracts include extracts obtained from plants by an ordinary method, such as *Angelica keiskei*, adzuki bean, avocado, hydrangea, *Gynostemma pentaphyllum*, altheca, arnica, almond, aloe, apricot, stinging nettle, iris, fennel, turmeric, *Rosa multiflora*, *Scutellaria baicalensis*, Phellodendri cortex, *Coptis japonica*, barley, okura, Saint-John's-wort, dead nettle, *Ononis spinosa*, *Nasturtium officinale*, persimmon, puerariae root, *Valeriana fauriei*, birch, cattail, chamomile, chamomilla, oats, licorice, raspberry, kiwi, cucumber, Armeniacae semen, kukui nut, Cape jasmine, *Sasa albo-marginata*, walnut, cinnamon, mulberry, Gunjo, gentian, cranesbill, burdock, sesame, wheat, rice, *Camellia sasanqua*, saffron, hawthorn, Japanese pepper tree, mushroom, *Rehmannia glutinosa*, Chicon, beefsteak plant, Japanese linden, *Filipendula multijuga*, peony, ginger, Japanese iris, white birch, *Lonicera japonica*, field horsetail, *Stevia rebaudiana*, western ivy, western hawthorn, black elder, *Juniperus communis*, *Achillea millefolium*, peppermint, sage, common mallow, *Cnidium officinale*, Japanese green gentian, soybean, Zizyphi fructus, thyme, tea, clove, dried orange peel, evening primrose, camellia, *Centella asiatica*, English walnut, *Angelica acutiloba*, *Calendula officinalis*, Persicae semen, Aurantii pericarpium, corn, *Houttuynia cordata*, tomato, carrot, garlic, wild rose, malt, parsley, rye, adlay, Japanese mint, papaya, hamamelis, rose, white cedar, sunflower, loquat, coltsfoot, grapes, placenta, hazelnut, dishcloth gourd, safflower, *Ficus religiosa*, *Paeonia suffruticosa*, hop, macadamia nut, pine, marronnier, melissa, melilot, peach, malt, Rodger's bronze leaf, palm, eucalyptus, creeping saxifrage, lily, *Coix lacryma-jobi* var. ma-yuen, mugwort, rye, peanut, lavender, apple, litchi, lettuce, lemon, Chinese milk vetch, rosemary, camomile, agrimony, Japanese catalpa, *Thujopsis dolabrata*, *Euphorbia lathyris*, *Rabdosia japonica*, Aurantii fructus immaturus, Senkishi, chickweed, *Spirodela polyrhiza*, *Artemisia capillaris*, ginkgo, Chinese belflower, chrysanthemum, *Sasa albo-marginata*, soapberry and weeping golden bell. Of them, an extract obtained from hamamelis, *Paeonia suffruticosa*, agrimony, Japanese catalpa, *Thujopsis dolabrata*, eucalyptus, ginger, *Euphorbia lathyris*, *Rabdosia japonica* or Aurantii fructus immaturus is preferred.

It is preferable that when these plant extracts are included, their content is from about 0.0001 to 2% by mass in terms of dry solid content based on the whole emulsion composition.

Examples of moisturizers include polyhydric alcohols having moisturizing effects, such as glycol, glycerol, glucose, maltose, maltitol, sucrose, fructose, xylitol, sorbitol, maltotriose, threitol, erythritol, starch-decomposed reduced alcohol and sorbitol; ethylene glycol, 1,4-butylene glycol, diglycerol, triglycerol, tetraglycerol, 1,3-butylene glycol, propylene glycol, dipropylene glycol, polyethylene glycol and 1,3-propanediol.

Furthermore, polyoxyethylene methyl glucoside such as methyl gluceth-10 and methyl gluceth-20, and polyoxypropylene methyl glucoside such as PPG-20 and methyl glucose ester may be used.

It is preferable that when these moisturizers are included, their content is from about 0.01 to 30% by mass based on the whole emulsion composition.

Examples of the anti-inflammatory agents include glycyrrhizinic acid and salts thereof, glycyrrhethinic acid and salts thereof, epsilon-aminocaproic acid and salts thereof, allantoin, lysozyme chloride, guaiazulene, methyl salicylate and γ-oryzanol. Of them, one or more selected from the group consisting of glycyrrhethinic acid, stearyl glycyrrhethinate and epsilon-aminocaproic acid are preferred.

It is preferable that when these anti-inflammatory agents are included, their content is from about 0.001 to 2% by mass based on the whole emulsion composition.

Examples of antiseptics include paraoxybenzoic acid esters (paraben) such as methyl paraben, dehydroacetic acid and a salt thereof and phenoxyethanol. Sodium benzoate, disodium edetate and the like may be used as an antiseptic auxiliary.

Furthermore, a thickener such as disteardimonium hectorite and dextrin palmitate may be used as another component.

It is preferable that in order to improve skin-protecting feeling and smoothness when applied to the skin, the emulsion composition of the present invention is an O1/W/O emulsion composition in which an inner oil phase O1 containing the components (A) to (D) or components (A) to (D) and (F) is dispersed in the aqueous phase of an W/O emulsion composition.

The external agent for the skin may include, for example, a known component other than the components (A) to (D) or the components (A) to (F) in the inner oil phase O1 to the extent that does not reduce the effect of the present invention. The content of solid lipid other than the components (A) to (D) or the components (A) to (F) is preferably 1% by mass or less, more preferably 0.5% by mass or less, further preferably 0.1% by mass or less, and substantially 0% by mass in the emulsion composition in order to suppress crystallization of a ceramide when stored at low temperature so as to compound a ceramide in a stable manner.

Furthermore, the ratio of the inner oil phase O1 in the O1/W/O emulsion composition is preferably from 0.1 to 15% by mass, more preferably from 0.5 to 12% by mass, further preferably from 1 to 10% by mass, and still more preferably from 2 to 8% by mass, and particularly preferably from 3.5 to 7% by mass based on the whole emulsion composition to improve emulsification stability of the emulsion composition.

Next, the aqueous phase in the W/O emulsion composition will be described.

For the ratio of the aqueous phase W in the emulsion composition, the aqueous phase W is the remainder excluding the outer oil phase O (the total of the outer oil phase O and the inner oil phase O1 in the case of an O1/W/O emulsion composition) from the emulsion composition; the ratio of the aqueous phase W is preferably from 30 to 90% by mass, and more preferably from 50 to 85% by mass based on the whole emulsion composition to improve emulsification stability of the emulsion composition.

Specifically, the aqueous phase W mainly contains water. The content of water in the emulsion composition is preferably from 30 to 90% by mass, and more preferably from 45 to 85% by mass based on the whole emulsion composition. The content of water may also be the remainder excluding the components other than water in the emulsion composition.

The aqueous phase may also contain a component other than water, specifically, a water-soluble components, out of the optional components and other components described later.

Next, the outer oil phase O in the O1/W/O emulsion composition will be described.

The ratio of the outer oil phase in the emulsion composition is preferably from 5 to 40% by mass, more preferably from 10 to 38% by mass, further preferably from 15 to 36% by mass, and still more preferably from 20 to 30% by mass in order to improve emulsification stability of the emulsion composition and improve feeling on use free from friction.

Furthermore, in the present embodiment, the ratio of the total mass of the inner oil phase and the aqueous phase to the mass of the outer oil phase in the O1/W/O emulsion composition, i.e., the ratio represented by ((O1+W)/O), is preferably from 1 to 19, more preferably from 1.5 to 10, and further preferably from 2 to 5 in order to improve emulsification stability of the emulsion composition.

Furthermore, in the present embodiment, the ratio of the total mass of the inner oil phase and the outer oil phase in the O1/W/O emulsion composition, i.e., the mass ratio represented by (O1+O) to the whole emulsion composition, (O1+O)/(O1+W+O), is preferably from 0.05 to 0.5, more preferably from 0.1 to 0.45, and further preferably from 0.15 to 0.4 in order to improve emulsification stability of the emulsion composition.

Next, the method for producing the emulsion composition in the present embodiment will be described.

A known producing method, for example, may be used to produce the W/O emulsion composition and the O1/W/O emulsion composition of the present embodiment. It is preferable that the O1/W/O emulsion composition is produced by a two-stage emulsifying method in order to improve emulsification stability of the emulsion composition. An inner phase O1/W emulsion composition which has been previously prepared by a common method is re-emulsified in an oil agent in which components of an outer oil phase are dissolved, swollen or dispersed to give a milky white, or transparent to semi-transparent O1/W/O emulsion composition.

The emulsion composition obtained according to the present embodiment may be formed into a cosmetic in various forms, e.g., emulsion, a cream such as a hair cream and a hand cream, an emulsified foundation and serum.

Furthermore, the emulsion composition of the present embodiment may be used by applying it to the skin excluding hair, preferably any of the face, the body or the limbs. The emulsion composition of the present embodiment may also be used for the scalp and hair.

Embodiments of the present invention have been described above, but the embodiments only illustrate the present invention, and various configurations other than the above may also be used.

For the above embodiments, the present invention also discloses the following compositions, methods of production and applications.

<1>
A W/O emulsion composition comprising the following components (A), (B), (C), (D) and (E):
  (A) a glycerol monofatty acid ester having 12 to 26 carbon atoms,
  (B) a higher alcohol having 10 to 22 carbon atoms,
  (C) a ceramide,
  (D) one or more selected from the group consisting of sphingosine, a salt thereof and an ionic surfactant, and
  (E) a nonionic surfactant comprising the following (e1) and (e2):
    (e1) one or more selected from the group consisting of a crosslinked polyether-modified silicone and a crosslinked polyglycerol-modified silicone, and
    (e2) one or more selected from the group consisting of a polyether-modified silicone, a polyglycerol-modified silicone and a polyglycerol fatty acid ester.

<2>
The W/O emulsion composition according to <1>, wherein the content of the component (e1) is preferably 0.1% by mass or more and 10% by mass or less, more preferably 0.5% by mass or more and 2% by mass or less, and further preferably 0.75% by mass or more and 1.5% by mass or less in the emulsion composition.

<3>
The W/O emulsion composition according to <1> or <2>, wherein a content of the component (e2) is preferably 0.1% by mass or more and 10% by mass or less, more preferably 2.5% by mass or more and 5% by mass or less, and further preferably 3% by mass or more and 4% by mass or less in the emulsion composition.

<4>
The W/O emulsion composition according to any one of <1> to <3>, wherein a mass ratio of a content of the component (e1) and a content of the component (e2), (e2/e1), is preferably 0.1 or more and 8 or less, more preferably 1 or more and 5 or less, and further preferably 3 or more and 5 or less.

<5>
The W/O emulsion composition according to any one of <1> to <4>, wherein an aqueous phase comprises the components (A) to (D).

<6>
The W/O emulsion composition according to any one of <1> to <5>, wherein the emulsion composition is an O1/W/O emulsion cosmetic composition in which an inner oil phase O1 is dispersed in an aqueous phase of the W/O emulsion composition, and the inner oil phase O1 comprises the components (A) to (D).

<7>
The W/O emulsion composition according to any one of <1> to <6>, wherein the component (D) is an anionic surfactant, and the emulsion composition further comprises (F) a nonionic surfactant other than (e1) or (e2), having an HLB of 8 or more and (G) one or more selected from the group consisting of an inorganic acid and an organic acid having 6 or less carbon atoms.

<8>
The W/O emulsion composition according to <7>, wherein a mass ratio of the component (F) to the component (G), (F/G), is preferably 0.3 or more and 6.0 or less, more preferably 0.7 or more and 5.5 or less, further preferably 1.0 or more and 5.0 or less, and still more preferably 1.2 or more and 4.0 or less <9>
The W/O emulsion composition according to <7> or <8>, wherein a mass ratio of the component (F) to the component (A), (F/A), is preferably 0.1 or more and 1.5 or less, more preferably 0.2 or more and 1.3 or less, and further preferably 0.25 or more and 1.0 or less.

<10>
The W/O emulsion composition according to any one of <7> to <9>, wherein an aqueous phase comprises the components (A) to (D), (F) and (G).

<11>
The W/O emulsion composition according to any one of <7> to <10>, wherein the emulsion composition is an O1/W/O emulsion cosmetic composition in which an inner oil phase O1 is dispersed in an aqueous phase of the W/O emulsion composition, and the inner oil phase O1 comprises the components (A) to (D) and (F).

<12>
The W/O emulsion composition according to any one of <7> to <11>, wherein the emulsion composition is an O1/W/O emulsion cosmetic in which an inner oil phase O1 is dispersed in an aqueous phase of the W/O emulsion composition, and the inner oil phase O1 comprises the components (A) to (D) and (F).

<13>
An O1/W/O emulsion cosmetic composition comprising the following components (A), (B), (C), (D) and (E):

(A) one or more selected from the group consisting of glycerol monobehenate, glycerol monostearate and glycerol monopalmitate;
(B) one or more selected from the group consisting of stearyl alcohol, cetyl alcohol and behenyl alcohol;
(C) a ceramide;
(D) one or more selected from the group consisting of sphingosine, a salt thereof, N-acylglutamate having 12 to 22 carbon atoms and N-alkyloyl methyl taurate having 12 to 22 carbon atoms; and
(E) a nonionic surfactant comprising the following (e1) and (e2):
(e1) one or more selected from the group consisting of a crosslinked polyether-modified silicone and a crosslinked polyglycerol-modified silicone; and
(e2) one or more selected from the group consisting of a polyether-modified silicone, a polyglycerol-modified silicone and a polyglycerol fatty acid ester, wherein an inner oil phase O1 is dispersed in an aqueous phase of the W/O emulsion composition and the inner oil phase O1 comprises the components (A) to (D).

<14>
An O1/W/O emulsion cosmetic composition comprising the following components (A), (B), (C), (D) and (E):
(A) one or more selected from the group consisting of glycerol monobehenate, glycerol monostearate and glycerol monopalmitate;
(B) one or more selected from the group consisting of stearyl alcohol, cetyl alcohol and behenyl alcohol;
(C) a ceramide;
(D) one or more selected from the group consisting of sphingosine, a salt thereof, N-acylglutamate having 12 to 22 carbon atoms and N-alkyloyl methyl taurate having 12 to 22 carbon atoms; and
(E) a nonionic surfactant comprising the following (e1) and (e2):
(e1) one or more selected from the group consisting of a crosslinked polyether-modified silicone and a crosslinked polyglycerol-modified silicone; and
(e2) one or more selected from the group consisting of a polyether-modified silicone, a polyglycerol-modified silicone and a polyglycerol fatty acid ester,
wherein a mass ratio of a content of the component (e1) and a content of the component (e2), (e2/e1), is 3 or more and 5 or less, and
an inner oil phase O1 is dispersed in an aqueous phase of the W/O emulsion composition, and the inner oil phase O1 comprises the components (A) to (D).

<15>
An O1/W/O emulsion cosmetic composition comprising the following components (A), (B), (C), (D) and (E):
(A) one or more selected from the group consisting of glycerol monobehenate, glycerol monostearate and glycerol monopalmitate;
(B) one or more selected from the group consisting of stearyl alcohol, cetyl alcohol and behenyl alcohol;
(C) a ceramide;
(D) one or more selected from the group consisting of sphingosine, a salt thereof, N-acylglutamate having 12 to 22 carbon atoms and N-alkyloyl methyl taurate having 12 to 22 carbon atoms; and
(E) a nonionic surfactant comprising the following (e1) and (e2):
(e1) one or more selected from the group consisting of a crosslinked polyether-modified silicone selected from the group consisting of (dimethicone/(PEG-10/15)) crosspolymer), (PEG-15/lauryl dimethicone) crosspolymer, (PEG-10/lauryl dimethicone) crosspolymer and (PEG-15/lauryl dimethicone) crosspolymer) and a crosslinked polyglycerol-modified silicone selected from the group consisting of (dimethicone/polyglycerol-3) crosspolymer and (lauryl dimethicone/polyglycerol-3) crosspolymer; and
(e2) one or more selected from the group consisting of PEG-3 dimethicone, PEG-10 dimethicone, PEG-12 dimethicone, PEG-11 methyl ether dimethicone, PEG-9 polydimethylsiloxyethyl dimethicone, cetyl PEG/PPG-10/1 dimethicone and diglycerol fatty acid ester,
wherein a mass ratio of a content of the component (e1) and a content of the component (e2), (e2/e1), is 0.1 or more and 8 or less,
an inner oil phase O1 is dispersed in an aqueous phase of the W/O emulsion composition, and the inner oil phase O1 comprises the components (A) to (D).

<16>
An O1/W/O emulsion cosmetic composition comprising the following components (A), (B), (C), (D) and (E):
(A) one or more selected from the group consisting of glycerol monobehenate, glycerol monostearate and glycerol monopalmitate;
(B) one or more selected from the group consisting of stearyl alcohol, cetyl alcohol and behenyl alcohol;
(C) a ceramide;
(D) one or more selected from the group consisting of sphingosine, a salt thereof, N-acylglutamate having 12 to 22 carbon atoms and N-alkyloyl methyl taurate having 12 to 22 carbon atoms; and
(E) a nonionic surfactant comprising the following (e1) and (e2):
(e1) one or more selected from the group consisting of a crosslinked polyether-modified silicone selected from the group consisting of (dimethicone/(PEG-10/15)) crosspolymer), (PEG-15/lauryl dimethicone) crosspolymer, (PEG-10/lauryl dimethicone) crosspolymer and (PEG-15/lauryl dimethicone) crosspolymer and a crosslinked polyglycerol-modified silicone selected from the group consisting of (dimethicone/polyglycerol-3) crosspolymer and (lauryl dimethicone/polyglycerol-3) crosspolymer; and (e2) one or more selected from the group consisting of PEG-3 dimethicone, PEG-10 dimethicone, PEG-12 dimethicone, PEG-11 methyl ether dimethicone, PEG-9 polydimethylsiloxyethyl dimethicone, cetyl PEG/PPG-10/1 dimethicone and diglycerol fatty acid ester,
wherein a mass ratio of a content of the component (e1) and a content of the component (e2), (e2/e1), is 3 or more and 5 or less,
an inner oil phase O1 is dispersed in an aqueous phase of the W/O emulsion composition, and the inner oil phase O1 comprises the components (A) to (D).

<17>
The O1/W/O emulsion cosmetic composition according to any one of <13> to <16>, wherein a content of the component (A) is from 0.2 to 10% by mass based on the whole emulsion composition; a content of the component (B) is from 0.2 to 10% by mass based on the whole emulsion composition; a content of the component (C) is from 0.5 to 10% by mass based on the whole emulsion composition; a content of the component (D) is from 0.05 to 5% by mass based on the whole emulsion composition; a content of the component (e1) is 0.1% by mass or more and 10% by mass or less based on the whole emulsion composition; and a content of the component (e2) is 0.1% by mass or more and to 10% by mass or less based on the whole emulsion composition.

<18>

The O1/W/O emulsion cosmetic composition according to any one of <13> to <16>, wherein a content of the component (A) is from 0.5 to 1.0% by mass based on the whole emulsion composition; a content of the component (B) is from 0.5 to 1.0% by mass based on the whole emulsion composition; a content of the component (C) is from 0.8 to 5% by mass based on the whole emulsion composition; a content of the component (D) is from 0.4 to 2% by mass based on the whole emulsion composition; a content of the component (e1) is 0.75% by mass or more and 1.5% by mass or less based on the whole emulsion composition; and a content of the component (e2) is 3% by mass or more and to 4% by mass or less based on the whole emulsion composition.

<19>

An O1/W/O emulsion cosmetic composition comprising the following components (A), (B), (C), (D), (E), (F) and (G):
- (A) one or more selected from the group consisting of glycerol monobehenate, glycerol monostearate and glycerol monopalmitate;
- (B) one or more selected from the group consisting of stearyl alcohol, cetyl alcohol and behenyl alcohol;
- (C) a ceramide;
- (D) one or more selected from the group consisting of N-acylglutamate having 12 to 22 carbon atoms or a salt thereof, and N-alkyloyl methyl taurate having 12 to 22 carbon atoms;
- (E) a nonionic surfactant comprising the following (e1) and (e2):
- (e1) one or more selected from the group consisting of a crosslinked polyether-modified silicone and a crosslinked polyglycerol-modified silicone; and
- (e2) one or more selected from the group consisting of a polyether-modified silicone, polyglycerol-modified silicone and polyglycerol fatty acid ester;
- (F) a nonionic surfactant other than (e1) or (e2), having an HLB of 8 or more and 20 or less; and
- (G) one or more selected from the group consisting of an inorganic acid and an organic acid having 6 or less carbon atoms, wherein an inner oil phase O1 is dispersed in an aqueous phase of the W/O emulsion composition and the inner oil phase O1 comprises the components (A) to (D) and (F).

<20>

An O1/W/O emulsion cosmetic composition comprising the following components (A), (B), (C), (D), (E), (F) and (G):
- (A) a glycerol monofatty acid ester having 12 to 26 carbon atoms;
- (B) a higher alcohol having 10 to 22 carbon atoms;
- (C) a ceramide;
- (D) one nonionic or more selected from the group consisting of N-acylglutamate having 12 to 22 carbon atoms or a salt thereof, and N-alkyloyl methyl taurate having 12 to 22 carbon atoms;
- (E) a nonionic surfactant comprising the following (e1) and (e2):
- (e1) one or more selected from the group consisting of a crosslinked polyether-modified silicone and a crosslinked polyglycerol-modified silicone; and
- (e2) one or more selected from the group consisting of a polyether-modified silicone, polyglycerol-modified silicone and polyglycerol fatty acid ester;
- (F) a nonionic surfactant other than (e1) or (e2), having an HLB of 8 or more and 20 or less; and
- (G) one or more organic or inorganic acids selected from the group consisting of malic acid, lactic acid, citric acid, succinic acid, glutamic acid, adipic acid and phosphoric acid, wherein an inner oil phase O1 is dispersed in an aqueous phase of the W/O emulsion composition and the inner oil phase O1 comprises the components (A) to (D) and (F).

<21>

An O1/W/O emulsion cosmetic composition comprising the following components (A), (B), (C), (D), (E), (F) and (G):
- (A) a glycerol monofatty acid ester having 12 to 26 carbon atoms;
- (B) a higher alcohol having 10 to 22 carbon atoms:
- (C) a ceramide;
- (D) N-alkyloyl methyl taurate having 16 to 20 carbon atoms;
- (E) a nonionic surfactant comprising the following (e1) and (e2):
- (e1) one or more selected from the group consisting of a crosslinked polyether-modified silicone and a crosslinked polyglycerol-modified silicone; and
- (e2) one or more selected from the group consisting of a polyether-modified silicone, polyglycerol-modified silicone and polyglycerol fatty acid ester;
- (F) a nonionic surfactant other than (e1) or (e2), having an HLB of 14 or more and 20 or less; and
- (G) one or more organic or inorganic acids selected from the group consisting of malic acid, lactic acid, citric acid, succinic acid, glutamic acid, adipic acid and phosphoric acid, wherein an inner oil phase O1 is dispersed in an aqueous phase of the W/O emulsion composition and the inner oil phase O1 comprises the components (A) to (D) and (F).

<22>

The O1/W/O emulsion composition according to <21>, wherein a content of the component (A) is from 0.2 to 10% by mass based on the whole emulsion composition; a content of the component (B) is from 0.2 to 10% by mass based on the whole emulsion composition; a content of the component (C) is from 0.5 to 10% by mass based on the whole emulsion composition; a content of the component (D) is from 0.05 to 5% by mass based on the whole emulsion composition; a content of the component (e1) is 0.1% by mass or more and 10% by mass or less based on the whole emulsion composition; a content of the component (e2) is 0.1% by mass or more and 10% by mass or less based on the whole emulsion composition; a content of the component (F) is from 0.05 to 1% by mass based on the whole emulsion composition; and a content of the component (G) is from 0.01 to 2% by mass based on the whole emulsion composition.

<23>

The O1/W/O emulsion cosmetic composition according to any one of <19> to <21>, wherein a content of the component (A) is from 0.5 to 1.0% by mass based on the whole emulsion composition; a content of the component (B) is from 0.5 to 1.0% by mass based on the whole emulsion composition; a content of the component (C) is from 0.8 to 5% by mass based on the whole emulsion composition; a content of the component (D) is from 0.4 to 2% by mass based on the whole emulsion composition; a content of the component (e1) is 0.75% by mass or more and 1.5% by mass or less based on the whole emulsion composition; a content of the component (e2) is 3% by mass or more and 4% by mass or less based on the whole emulsion composition; a content of the component (F) is from 0.2 to 0.7% by mass based on the whole emulsion composition; and a content of the component (G) is from 0.1 to 0.2% by mass based on the whole emulsion composition.

EXAMPLES

Examples 1 to 21 and Comparative Examples 1 to 4

Emulsion compositions having the composition shown in Tables 1 to 4 were produced and their temperature cycle stability and feeling on use (thickness and spreadability) were evaluated by the methods described below. The results are also shown in Tables 1 to 4.

(Method of Production)

The emulsion composition of the respective Examples was produced by the following steps.
 (1) The components (A) to (D) and polyhydric alcohol were mixed and dissolved at 80° C. until homogeneous.
 (2) Water and other components of an aqueous phase were mixed and dissolved at 80° C. until homogeneous.
 (3) The mixture obtained in (2) was added to the mixture obtained in (1) and an O/W emulsion composition was prepared by phase inversion emulsification, and then the composition was allowed to cool to room temperature (25° C.).
 (4) Components of outer oil phase were mixed at room temperature until homogeneous.
 (5) The mixture obtained in (3) was added to the mixture obtained in (4) and the resultant was emulsified by stirring until homogeneous to give an O/W/O emulsion composition.

(Method of Evaluation)

(Temperature Cycle Stability)

50 g of the respective emulsion compositions was put in a polypropylene container and the container was sealed and stored in a cycle (per day) of being stored in a storage at 50° C. for 12 hours and stored in a storage at −5° C. for 12 hours. The compositions were evaluated according to the following criteria.
 A: Kept in an emulsified state for 15 days or more.
 B: Separated in 8 to 14 days.
 C: Separated in 4 to 7 days.
 D: Separated in 1 to 3 days.
 E: Separated in less than a day (Feeling on Use)

For the feeling on use when a cosmetic made of the emulsion composition prepared in the respective Examples was applied to the inside of the forearm, thickness and spreadability were evaluated by three expert panelists. The panelists evaluated the respective items by the following criteria. The average value of the scores given by the three panelists was calculated.

(Thickness)

The criteria include 5 scales: those with very excellent thickness were rated as 5, those with excellent thickness were rated as 4, those with thickness were rated as 3, those with no thickness were rated as 2, and those with no thickness at all and which could not be practically used were rated as 1.

(Spreadability)

The criteria include 5 scales: those with very excellent spreadability were rated as 5, those with excellent spreadability were rated as 4, those with spreadability were rated as 3, those with no spreadability were rated as 2, and those with no spreadability at all and which could not be practically used were rated as 1.

The components used, which are described in the tables, are as follows.
 *1: Sunsoft NO. 8100 manufactured by Taiyo International
 *2: Cetyl alcohol NX manufactured by Kokyu Alcohol Kogyo Co., Ltd.
 *3: SOFCARE SL-E manufactured by Kao Corporation
 *4: NIKKOL SMT manufactured by Nikko Chemicals Co., Ltd.
 *5: 86% glycerol manufactured by Kao Corporation
 *6: PARLEAM EX manufactured by NOF Corporation
 *7: KSG-210 manufactured by Shin-Etsu Chemical Co., Ltd. (active ingredient 25%)
 *8: KF-6017P manufactured by Shin-Etsu Chemical Co., Ltd.
 *9: COSMOL 42V manufactured by The Nisshin Oillio Group Ltd.
 *10: Phytosphingosine manufactured by Evonik Industries AG
 *11: PURE L-GLUTAMIC ACID manufactured by AJINOMOTO FOODS EUROPE SAS
 *12: KSG-310 manufactured by Shin-Etsu Chemical Co., Ltd. (active ingredient 30%)
 *13: KSG-710 manufactured by Shin-Etsu Chemical Co., Ltd. (active ingredient 25%)
 *14: KF-6015 manufactured by Shin-Etsu Chemical Co., Ltd.
 *15: EMANON CH-60 manufactured by Kao Corporation
 *16: *Eucalyptus* extract K manufactured by KOEI KOGYO CO., LTD.
 *17: Asunaro Liquid K-B manufactured by ICHIMARU PHARCOS Co., Ltd.
 *18: Silicone KF-96L-2CS manufactured by Shin-Etsu Chemical Co., Ltd.
 *19: Rheopearl KL2 manufactured by Chiba Flour Milling Co., Ltd.
 *20: EMALEX HC-5 manufactured by Nihon Emulsion Co., Ltd.
 *21: Concentrated glycerol for cosmetic manufactured by Kao Corporation
 *22: EMANON CH-25 manufactured by Kao Corporation
 *23: EMULGEN 1620G manufactured by Kao Corporation
 *24: EMANON 3199V manufactured by Kao Corporation
 *25: RHEODOL 460V manufactured by Kao Corporation
 *26: RHEODOL TW-S320V manufactured by Kao Corporation
 *27: EMALEX HC-10 manufactured by Nihon-Emulsion Co., Ltd.

TABLE 1

|  |  |  | Example | | | Comparative Example | | | |
| --- | --- | --- | --- | --- | --- | --- | --- | --- | --- |
|  |  |  | 1 | 2 | 3 | 1 | 2 | 3 | 4 |
| Inner oil phase O1 | (A) | Behenic acid monoglyceride*1 | 0.6 | 0.6 | 0.6 | 0.6 | 0.6 | 0.6 | 0.6 |
|  | (B) | Cetyl alcohol*2 | 0.6 | 0.6 | 0.6 | 0.6 | 0.6 | 0.6 | 0.6 |
|  | (C) | Pseudo-ceramide*3 | 3 | 3 | 3 | 3 | 3 | 3 | 3 |
|  | (D) | Na N-stearoyl methyl taurate*4 | 0.5 | 0.5 | 0.5 | 0.5 | 0.5 | 0.5 | 0.5 |
| Aqueous phase |  | Glycerol*5 | 17.2 | 17.2 | 17.2 | 17.2 | 17.2 | 17.2 | 17.2 |
|  |  | Methyl paraben | 0.3 | 0.3 | 0.3 | 0.3 | 0.3 | 0.3 | 0.3 |
|  |  | Water | Balance | Balance | Balance | Balance | Balance | Balance | Balance |
| Outer oil phase O |  | Hydrogenated polyisobutene*6 | 17.5 | 17.5 | 17.5 | 20.5 | 7 | 20.5 | 20.5 |
|  | (E)(e1) | (Dimeticone/(PEG-10/15)) crosspolymer*7 | 4.00 | 4.00 | 4.00 | — | 18.00 | — | — |
|  |  | Actual content of (e1) | 1.00 | 1.00 | 1.00 | — | 4.50 | — | — |
|  | (E)(e2) | PEG-10 dimethicone*8 | 1.50 | 3.50 | — | 2.25 | — | 4.50 | — |
|  | (E)(e2) | Polyglyceryl diisostearate*9 | 2.00 | — | 3.50 | 2.25 | — | — | 4.50 |
|  |  | Total | 100 | 100 | 100 | 100 | 100 | 100 | 100 |
|  |  | Total amount of active agents (active ingredients) | 4.5 | 4.5 | 4.5 | 4.5 | 4.5 | 4.5 | 4.5 |
|  |  | (e2)/(e1) | 3.5 | 3.5 | 3.5 | — | — | — | — |
|  |  | Stability under temperature cycle conditions | A | A | B | E | D | E | E |
|  | Feeling on use | Thickness | 5.0 | 4.3 | 3.3 | 5.0 | 2.0 | 4.0 | 2.3 |
|  |  | Spreadability | 4.3 | 4.0 | 5.0 | 4.0 | 4.3 | 4.0 | 4.6 |

TABLE 2

|  |  |  | Example | | | | | | |
| --- | --- | --- | --- | --- | --- | --- | --- | --- | --- |
|  |  |  | 1 | 4 | 5 | 6 | 7 | 8 | 9 |
| Inner oil phase O1 | (A) | Behenic acid monoglyceride*1 | 0.6 | 0.6 | 0.6 | 0.6 | 0.6 | 0.6 | 0.6 |
|  | (B) | Cetyl alcohol*2 | 0.6 | 0.6 | 0.6 | 0.6 | 0.6 | 0.6 | 0.6 |
|  | (C) | Pseudo-ceramide*3 | 3 | 3 | 3 | 3 | 3 | 3 | 3 |
|  | (D) | Na N-stearoyl methyl taurate*4 | 0.5 | 0.5 | 0.5 | 0.5 | 0.5 | 0.5 | 0.5 |
| Aqueous phase |  | Glycerol*5 | 17.2 | 17.2 | 17.2 | 17.2 | 17.2 | 17.2 | 17.2 |
|  |  | Methyl paraben | 0.3 | 0.3 | 0.3 | 0.3 | 0.3 | 0.3 | 0.3 |
|  |  | Water | Balance | Balance | Balance | Balance | Balance | Balance | Balance |
| Outer oil phase O |  | Hydrogenated polyisobutene*6 | 17.5 | 21.25 | 22 | 13.75 | 10 | 16 | 14.5 |
|  | (E)(e1) | (Dimethicone/(PEG-10/15)) crosspolymer*7 | 4.00 | 2.00 | 2.00 | 6.00 | 8.00 | 6.00 | 8.00 |
|  |  | Actual content of (e1) | 1.00 | 0.50 | 0.50 | 1.50 | 2.00 | 1.50 | 2.00 |
|  | (E)(e2) | PEG-10 dimethicone*8 | 1.50 | 0.75 | 0.50 | 2.25 | 3.00 | 1.25 | 1.10 |
|  | (E)(e2) | Polyglyceryl diisostearate*9 | 2.00 | 1.00 | 0.50 | 3.00 | 4.00 | 1.75 | 1.40 |
|  |  | Total | 100 | 100 | 100 | 100 | 100 | 100 | 100 |
|  |  | Total amount of active agents (active ingredients) | 4.5 | 2.25 | 1.5 | 6.75 | 9 | 4.5 | 4.5 |
|  |  | (e2)/(e1) | 3.5 | 3.5 | 2.0 | 3.5 | 3.5 | 2.0 | 1.3 |
|  |  | Stability under temperature cycle conditions | A | A | C | A | A | A | A |
|  | Feeling on use | Thickness | 5.0 | 4.3 | 3.3 | 5.0 | 5.0 | 5.0 | 5.0 |
|  |  | Spreadability | 4.3 | 5.0 | 5.0 | 3.0 | 2.0 | 4.0 | 4.3 |

|  |  |  | Example | | | | | |
| --- | --- | --- | --- | --- | --- | --- | --- | --- |
|  |  |  | 10 | 11 | 12 | 13 | 14 | 15 |
| Inner oil phase O1 | (A) | Behenic acid monoglyceride*1 | 0.6 | 0.6 | 0.6 | 0.6 | 0.6 | 0.6 |
|  | (B) | Cetyl alcohol*2 | 0.6 | 0.6 | 0.6 | 0.6 | 0.6 | 0.6 |
|  | (C) | Pseudo-ceramide*3 | 3 | 3 | 3 | 3 | 3 | 3 |
|  | (D) | Na N-stearoyl methyl taurate*4 | 0.5 | 0.5 | 0.5 | 0.5 | 0.5 | 0.5 |
| Aqueous phase |  | Glycerol*5 | 17.2 | 17.2 | 17.2 | 17.2 | 17.2 | 17.2 |
|  |  | Methyl paraben | 0.3 | 0.3 | 0.3 | 0.3 | 0.3 | 0.3 |
|  |  | Water | Balance | Balance | Balance | Balance | Balance | Balance |
| Outer oil phase O |  | Hydrogenated polyisobutene*6 | 18.1 | 19 | 17.5 | 17.5 | 17.5 | 17.5 |
|  | (E)(e1) | (Dimethicone/(PEG-10/15)) crosspolymer*7 | 3.20 | 2.00 | 4.00 | 4.00 | 4.00 | 4.00 |
|  |  | Actual content of (e1) | 0.80 | 0.50 | 1.00 | 1.00 | 1.00 | 1.00 |
|  | (E)(e2) | PEG-10 dimethicone*8 | 1.60 | 1.70 | 1.00 | 0.50 | 1.75 | 2.50 |
|  | (E)(e2) | Polyglyceryl diisostearate*9 | 2.10 | 2.30 | 2.50 | 3.00 | 1.75 | 1.00 |
|  |  | Total | 100 | 100 | 100 | 100 | 100 | 100 |
|  |  | Total amount of active agents (active ingredients) | 4.5 | 4.5 | 4.5 | 4.5 | 4.5 | 4.5 |
|  |  | (e2)/(e1) | 4.6 | 8.0 | 3.5 | 3.5 | 3.5 | 3.5 |
|  |  | Stability under temperature cycle conditions | A | C | A | A | A | A |
|  | Feeling on use | Thickness | 5.0 | 5.0 | 4.3 | 4.0 | 5.0 | 5.0 |
|  |  | Spreadability | 4.3 | 4.3 | 4.3 | 5.0 | 4.3 | 4.0 |

TABLE 3

| | | | Example | | | | |
|---|---|---|---|---|---|---|---|
| | | | 1 | 16 | 17 | 18 | 19 |
| Inner oil phase O1 | (A) | Behenic acid monoglyceride*1 | 0.6 | 0.6 | 0.6 | 0.6 | 0.6 |
| | (B) | Cetyl alcohol*2 | 0.6 | 0.6 | 0.6 | 0.6 | 0.6 |
| | (C) | Pseudo-ceramide*3 | 3 | 3 | 3 | 3 | 3 |
| | (D) | Na N-stearoyl methyl taurate*4 | 0.5 | — | 0.5 | 0.5 | 0.5 |
| | (D) | Phytosphingosine*10 | — | 0.15 | — | — | — |
| Aqueous phase | | Glycerol*5 | 17.2 | 17.2 | 17.2 | 17.2 | 17.2 |
| | | Methyl paraben | 0.3 | 0.3 | 0.3 | 0.3 | 0.3 |
| | | Glutamic acid*11 | — | 0.1 | — | — | — |
| | | Water | Balance | Balance | Balance | Balance | Balance |
| Outer oil phase O | | Hydrogenated polyisobutene*6 | 17.5 | 17.5 | 18.2 | 17.5 | 17.5 |
| | (E)(e1) | (Dimethicone/(PEG-10/15)) crosspolymer*7 | 4.00 | 4.00 | — | — | 4.00 |
| | | (PEG-15/lauryl dimethicone) crosspolymer*12 | — | — | 3.30 | — | — |
| | | (Dimethicone/polyglycerol-3) crosspolymer*13 | — | — | — | 4.00 | — |
| | | Actual content of (e1) | 1.00 | 1.00 | 1.00 | 1.00 | 1.00 |
| | (E)(e2) | PEG-10 dimethicone*8 | 1.50 | 1.50 | 1.50 | 1.50 | — |
| | | PEG-3 dimethicone*14 | — | — | — | — | 1.50 |
| | | Polyglyceryl diisostearate*9 | 2.00 | — | 2.00 | 2.00 | 2.00 |
| | | Total | 100 | 100 | 100 | 100 | 100 |
| | | Total amount of active agents (active ingredients) | 100 | 100 | 100 | 100 | 100 |
| | | (e2)/(e1) | 3.5 | 3.5 | 3.5 | 3.5 | 3.5 |
| | | Stability under temperature cycle conditions | A | A | B | B | B |
| Feeling on use | | Thickness | 5.0 | 5.0 | 4.3 | 4.3 | 3.3 |
| | | Spreadability | 4.3 | 4.3 | 4.3 | 4.3 | 5.0 |

TABLE 4

| | | | Example | |
|---|---|---|---|---|
| | | | 20 | 21 |
| Inner oil phase O1 | (A) | Behenic acid monoglyceride*1 | 0.6 | 0.6 |
| | (B) | Cetyl alcohol*2 | 0.6 | 0.6 |
| | (C) | Pseudo-ceramide*3 | 3.3 | 3.3 |
| | (D) | Na N-stearoyl methyl taurate*4 | 0.5 | — |
| | | Phytosphingosine*10 | — | 0.15 |
| | (F) | PEG-60 hydrogenated castor oil*15 | 0.2 | — |
| Aqueous phase | (G) | Succinic acid | 0.15 | — |
| | | 48% sodium hydroxide solution | 0.07 | — |
| | | Glutamic acid*11 | — | 0.1 |
| | | Glycerol*5 | 17.2 | 17.2 |
| | | Methyl paraben | 0.3 | 0.3 |
| | | Allantoin | 0.5 | 0.5 |
| | | Eucalyptus globulus leaf extract*16 | 0.3 | 0.3 |
| | | Thujopsis dolabrata branch extract*17 | 2 | 2 |
| | | Water | Balance | Balance |
| Outer oil phase O | | Hydrogenated polyisobutene*6 | 12 | 17.6 |
| | | Dimethicone*18 | 5.0 | — |
| | (E)(e1) | (Dimethicone/(PEG-10/15)) crosspolymer*7 | 4.00 | 4.00 |
| | | Actual content of (e1) | 1.00 | 1.00 |
| | (E)(e2) | PEG-10 dimethicone*8 | 1.50 | 1.50 |
| | (E)(e2) | Polyglyceryl diisostearate *9 | 2.00 | 2.00 |
| | | Dextrin palmitate*19 | 0.8 | 0.8 |
| | | Total | 100.0 | 100.0 |
| | | Total amount of active agents (active ingredients) | 4.5 | 4.5 |
| | | (e2)/(e1) | 3.5 | 3.5 |
| | | Stability under temperature cycle conditions | A | A |
| Feeling on use | | Thickness | 5.0 | 5.0 |
| | | Spreadability | 5.0 | 4.3 |

Examples 22 to 32 and Comparative Examples 5 to 10

Emulsion compositions having the composition shown in Tables 5 to 8 were produced and their high temperature stability (60° C.) and feeling on use (lastingness of moist feeling, thickness when applied, skin-protecting feeling, absence of friction when applied, and smoothness of skin) were evaluated by the methods described below. The results are also shown in Tables 5 to 8. The pH of the aqueous phase in Examples 22 to 32 and Comparative Examples 5 to 10 was all 4.5.

(Method of Production)

The emulsion composition of the respective Examples was produced by the following steps.

(1) The components (A) to (D), (F) and polyhydric alcohol were mixed and dissolved at 80° C. until homogeneous.

(2) Water and other components of an aqueous phase were mixed and dissolved at 80° C. until homogeneous.

(3) The mixture obtained in (2) was added to the mixture obtained in (1) and an O/W emulsion composition was prepared by phase inversion emulsification, and then the composition was allowed to cool to room temperature (25° C.).

(4) Components of an outer oil phase were mixed at room temperature until homogeneous.

(5) The mixture obtained in (3) was added to the mixture obtained in (4) and the resultant was emulsified by stirring until homogeneous to give an O/W/O emulsion composition.

(Method of Evaluation)
(High Temperature Stability)
(Emulsification Stability (Visual Observation))

40 g of the respective emulsion compositions was put in a polypropylene container and the condition after being stored at 60° C. for 10 days was visually observed and evaluated according to the following criteria.
 b: Kept in an emulsified state
 c: Kept in an emulsified state as a whole with a very little separation
 d: Separation observed
(Viscosity Stability)
The viscosity before storage and after storage at 60° C. of the respective emulsion compositions was measured by a B8R viscometer (Rotor No. T-C, 5 rpm, 60 seconds). The ratio of viscosity before and after storage (after storage/before storage) is shown according to the following criteria.
 b: Less than 1.5 times
 c: 1.5 times or more and less than 3 times
 d: 3 times or more
(Feeling on Use)
For the feeling on use when a cosmetic made of the emulsion composition prepared in the respective Examples was applied to the inside of the forearm, lastingness of moist feeling, thickness when applied, skin-protecting feeling, absence of friction when applied, and smoothness of the skin were evaluated. The individual panelists evaluated the respective items by the following criteria and after discussion the final score was determined.
(Lastingness of Moist Feeling)
The criteria include 4 scales: those with significant moist feeling were rated as 4, those with moist feeling were rated as 3, those with a little moist feeling were rated as 2, and those with no moist feeling and which could not be practically used were rated as 1.

(Thickness when Applied)
The criteria include 4 scales: those with significant thickness were rated as 4, those with thickness were rated as 3, those with a little thickness were rated as 2, and those with no thickness and which could not be practically used were rated as 1.

(Skin-Protecting Feeling)
The criteria include 4 scales: those with significant skin-protecting feeling were rated as 4, those with skin-protecting feeling were rated as 3, those with a little skin-protecting feeling were rated as 2, and those with no skin-protecting feeling and which could not be practically used were rated as 1.

(Absence of Friction when Applied)
The criteria include 4 scales: those without any friction were rated as 4, those with a little friction were rated as 3, those with friction but which could be used were rated as 2, and those with significant friction and uncomfortable feeling and which could not be practically used were rated as 1.

(Smoothness of Skin)
The criteria include 4 scales: those with significant smoothness of the skin were rated as 4, those with smoothness of the skin were rated as 3, those with a little smoothness of the skin were rated as 2, and those with no smoothness of the skin and which could not be practically used were rated as 1.

TABLE 5

| | | | Example | Comparative Example | |
|---|---|---|---|---|---|
| | | | 22 | 5 | 6 |
| Inner oil phase O1 | (A) | Behenic acid monoglyceride*1 | 0.6 | 0.6 | 0.6 |
| | (B) | Cetyl alcohol*2 | 0.6 | 0.6 | 0.6 |
| | (C) | Pseudo-ceramide*3 | 3.3 | 3.3 | 3.3 |
| | (D) | Na N-stearoyl methyl taurate*4 | 0.5 | 0.5 | 0.5 |
| | (F) | PEG-60 hydrogenated castor oil (HLB: 14)*15 | 0.2 | — | — |
| | | PEG-5 hydrogenated castor oil (HLB: 5)*20 | — | — | 0.2 |
| Aqueous phase | (G) | Succinic acid | 0.15 | 0.15 | 0.15 |
| | | 48% sodium hydroxide solution | 0.07 | 0.07 | 0.07 |
| | | Glycerol*21 | 17 | 17 | 17 |
| | | Methyl paraben | 0.3 | 0.3 | 0.3 |
| | | Water | Balance | Balance | Balance |
| Outer oil phase O | | Hydrogenated polyisobutene*6 | 17 | 17 | 17 |
| | (E)(e1) | (Dimethicone/(PEG-10/15)) crosspolymer*7 | 4.0 | 4.0 | 4.0 |
| | | Actual content of (e1) | 1.0 | 1.0 | 1.0 |
| | (e2) | Polyglyceryl diisostearate*9 | 3.5 | 3.5 | 3.5 |
| | | Dextrin palmitate*19 | 0.8 | 0.8 | 0.8 |
| | | Total | 100 | 100 | 100 |
| | | (F)/(G) | 1.33 | 0 | 0 |
| | | (F)/(A) | 0.33 | 0 | 0 |
| Initial physical properties | | Initial viscosity (dPa·s) | 678 | 567 | 629 |
| High temperature stability | | Viscosity after stored at 60° C. (dPa·s) | 570 | 1762 | 1477 |
| | | Ratio of viscosity after stored at 60° C./initial viscosity | 0.8 | 3.1 | 2.3 |
| | | Viscosity stability | b | d | c |
| | | Emulsification stability | b | d | d |
| Feeling on use | | Lastingness of moist feeling | 4 | 4 | 4 |
| | | Thickness when applied | 4 | 4 | 4 |
| | | Skin-protecting feeling | 4 | 4 | 4 |
| | | Absence of friction when applied | 4 | 4 | 4 |
| | | Smoothness of skin | 4 | 4 | 4 |

TABLE 6

|  |  |  | Example |  |  |  |
|---|---|---|---|---|---|---|
|  |  |  | 23 | 24 | 25 | 26 |
| Inner oil phase O1 | (A) | Behenic acid monoglyceride*1 | 0.6 | 0.6 | 0.6 | 0.6 |
|  | (B) | Cetyl alcohol*2 | 0.6 | 0.6 | 0.6 | 0.6 |
|  | (C) | Pseudo-ceramide*3 | 3.3 | 3.3 | 3.3 | 3.3 |
|  | (D) | Na N-stearoyl methyl taurate*4 | 0.5 | 0.5 | 0.5 | 0.5 |
|  | (F) | PEG-60 hydrogenated castor oil (HLB: 14)*15 | 0.1 | 0.2 | 0.5 | — |
|  |  | PEG-25 hydrogenated castor oil (HLB: 10.7)*22 | — | — | — | 0.8 |
| Aqueous phase | (G) | Succinic acid | 0.15 | 0.15 | 0.15 | 0.15 |
|  |  | 48% sodium hydroxide solution | 0.07 | 0.07 | 0.07 | 0.07 |
|  |  | Glycerol*22 | 17 | 17 | 17 | 17 |
|  |  | Methyl paraben | 0.3 | 0.3 | 0.3 | 0.3 |
|  |  | Water | Balance | Balance | Balance | Balance |
| Outer oil phase O | | Hydrogenated polyisobutene*6 | 17 | 17 | 17 | 17 |
|  | (E)(e1) | (Dimethicone/(PEG-10/15)) crosspolymer*7 | 4.0 | 4.0 | 4.0 | 4.0 |
|  |  | Actual content of (e1) | 1.0 | 1.0 | 1.0 | 1.0 |
|  | (e2) | PEG-10 dimethicone*8 | 1.5 | 1.5 | 1.5 | 1.5 |
|  | (e2) | Polyglyceryl diisostearate*9 | 2.0 | 2.0 | 2.0 | 2.0 |
|  |  | Dextrin palmitate*19 | 0.8 | 0.8 | 0.8 | 0.8 |
|  |  | Total | 100 | 100 | 100 | 100 |
|  |  | (F)/(G) | 0.67 | 1.33 | 3.33 | 5.33 |
|  |  | (F)/(A) | 0.17 | 0.33 | 0.83 | 1.33 |
| Initial physical properties | | Initial viscosity (dPa · s) | 1156 | 876 | 1025 | 985 |
| High temperature stability | | Viscosity after stored at 60° C. (dPa · s) | 2047 | 734 | 828 | 1604 |
|  |  | Ratio of viscosity after stored at 60° C./initial viscosity | 1.8 | 0.8 | 0.8 | 1.6 |
|  |  | Viscosity stability | c | b | b | c |
|  |  | Emulsification stability | c | b | b | c |
| Feeling on use | | Lastingness of moist feeling | 4 | 4 | 4 | 4 |
|  |  | Thickness when applied | 3 | 4 | 4 | 4 |
|  |  | Skin-protecting feeling | 4 | 4 | 4 | 4 |
|  |  | Absence of friction when applied | 3 | 3 | 3 | 3 |
|  |  | Smoothness of skin | 4 | 4 | 4 | 3 |

TABLE 7

|  |  |  | Example |  |  |  |  | Comparative Example |
|---|---|---|---|---|---|---|---|---|
|  |  |  | 27 | 28 | 29 | 30 | 31 | 7 |
| Inner oil phase O1 | (A) | Behenic acid monoglyceride*1 | 0.6 | 0.6 | 0.6 | 0.6 | 0.6 | 0.6 |
|  | (B) | Cetyl alcohol*2 | 0.6 | 0.6 | 0.6 | 0.6 | 0.6 | 0.6 |
|  | (C) | Pseudo-ceramide*3 | 3.3 | 3.3 | 3.3 | 3.3 | 3.3 | 3.3 |
|  | (D) | Na N-stearoyl methyl taurate*4 | 0.5 | 0.5 | 0.5 | 0.5 | 0.5 | 0.5 |
|  | (F) | PEG-25 hydrogenated castor oil (HLB: 10.7)*22 | 0.2 | — | — | — | — | — |
|  |  | Isoceteth-20 (HLB: 14)*23 | — | 0.2 | — | — | — | — |
|  |  | PEG-150 stearate (HLB: 19.4)*24 | — | — | 0.2 | — | — | — |
|  |  | Sorbeth-60 tetraoleate (HLB: 13.8)*25 | — | — | — | 0.2 | — | — |
|  |  | Polysorbate 65 (HLB: 10.5)*26 | — | — | — | — | 0.2 | — |
|  |  | PEG-10 hydrogenated castor oil (HLB: 7)*27 | — | — | — | — | — | 0.2 |
| Aqueous phase | (G) | Succinic acid | 0.15 | 0.15 | 0.15 | 0.15 | 0.15 | 0.15 |
|  |  | 48% sodium hydroxide solution | 0.07 | 0.07 | 0.07 | 0.07 | 0.07 | 0.07 |
|  |  | Glycerol*22 | 17 | 17 | 17 | 17 | 17 | 17 |
|  |  | Methyl paraben | 0.3 | 0.3 | 0.3 | 0.3 | 0.3 | 0.3 |
|  |  | Water | Balance | Balance | Balance | Balance | Balance | Balance |
| Outer oil phase O | | Hydrogenated polyisobutene*6 | 17 | 17 | 17 | 17 | 17 | 17 |
|  | (E)(e1) | (Dimethicone/(PEG-10/15)) crosspolymer*7 | 4.0 | 4.0 | 4.0 | 4.0 | 4.0 | 4.0 |
|  |  | Actual content of (e1) | 1.0 | 1.0 | 1.0 | 1.0 | 1.0 | 1.0 |
|  | (e2) | PEG-10 dimethicone*8 | 1.5 | 1.5 | 1.5 | 1.5 | 1.5 | 1.5 |
|  | (e2) | Polyglyceryl diisostearate*9 | 2.0 | 2.0 | 2.0 | 2.0 | 2.0 | 2.0 |
|  |  | Dextrin palmitate*19 | 0.8 | 0.8 | 0.8 | 0.8 | 0.8 | 0.8 |
|  |  | Total | 100 | 100 | 100 | 100 | 100 | 100 |
|  |  | (F)/(G) | 1.33 | 1.33 | 1.33 | 1.33 | 1.33 | 1.33 |
|  |  | (F)/(A) | 0.33 | 0.33 | 0.33 | 0.33 | 0.33 | 0.33 |

TABLE 7-continued

|  |  | Example | | | | | Comparative Example |
|---|---|---|---|---|---|---|---|
|  |  | 27 | 28 | 29 | 30 | 31 | 7 |
| Initial physical properties | Initial viscosity (dPa · s) | 1192 | 832 | 733 | 1060 | 873 | 975 |
| High temperature stability | Viscosity after stored at 60° C. (dPa · s) | 1348 | 1080 | 944 | 2043 | 2550 | 3835 |
|  | Ratio of viscosity after stored at 60° C./initial viscosity | 1.1 | 1.3 | 1.3 | 1.9 | 2.9 | 3.9 |
|  | Viscosity stability | b | b | b | c | c | d |
|  | Emulsification stability | b | b | b | b | b | b |
| Feeling on use | Lastingness of moist feeling | 4 | 4 | 4 | 4 | 4 | 4 |
|  | Thickness when applied | 4 | 4 | 4 | 4 | 3 | 4 |
|  | Skin-protecting feeling | 4 | 4 | 4 | 4 | 4 | 4 |
|  | Absence of friction when applied | 3 | 3 | 3 | 3 | 3 | 3 |
|  | Smoothness of skin | 4 | 4 | 4 | 3 | 3 | 3 |

TABLE 8

|  |  |  | Example | Comparative Example | | |
|---|---|---|---|---|---|---|
|  |  |  | 32 | 8 | 9 | 10 |
| Inner oil phase O1 | (A) | Behenic acid monoglyceride*1 | 0.6 | — | 0.6 | 0.6 |
|  | (B) | Cetyl alcohol*2 | 0.6 | 0.6 | — | 0.6 |
|  | (C) | Pseudo-ceramide*3 | 3.3 | 3.3 | 3.3 | 3.3 |
|  | (D) | Na N-stearoyl methyl taurate*4 | 0.5 | 0.5 | 0.5 | — |
|  | (F) | PEG-60 hydrogenated castor oil (HLB: 14)*15 | 0.2 | 0.2 | 0.2 | 0.2 |
| Aqueous phase | (G) | Succinic acid | 0.15 | 0.15 | 0.15 | 0.15 |
|  |  | 48% sodium hydroxide solution | 0.07 | 0.07 | 0.07 | 0.07 |
|  |  | Glycerol*22 | 17 | 17 | 17 | 17 |
|  |  | Methyl paraben | 0.3 | 0.3 | 0.3 | 0.3 |
|  |  | Allantoin | 0.5 | 0.5 | 0.5 | 0.5 |
|  |  | Eucalyptus globulus leaf extract*16 | 0.3 | 0.3 | 0.3 | 0.3 |
|  |  | Thujopsis dolabrata branch extract*17 | 2 | 2 | 2 | 2 |
|  |  | Water | Balance | Balance | Balance | Balance |
| Outer oil phase O |  | Hydrogenated polyisobutene*6 | 12 | 12 | 12 | 12 |
|  |  | Dimethicone*18 | 5 | 5 | 5 | 5 |
|  | (E)(e1) | (Dimethicone/(PEG-10/15)) crosspolymer*7 | 4.0 | 4.0 | 4.0 | 4.0 |
|  |  | Actual content of (e1) | 1.0 | 1.0 | 1.0 | 1.0 |
|  | (e2) | PEG-10 dimethicone*8 | 1.5 | 1.5 | 1.5 | 1.5 |
|  | (e2) | Polyglyceryl diisostearate*9 | 2.0 | 2.0 | 2.0 | 2.0 |
|  |  | Dextrin palmitate*19 | 0.8 | 0.8 | 0.8 | 0.8 |
|  |  | Total | 100.0 | 100.0 | 100 | 100 |
|  |  | (F)/(G) | 1.33 | 1.33 | 1.33 | 1.33 |
|  |  | (F)/(A) | 0.33 | — | 0.33 | 0.33 |
| Initial physical properties | Initial viscosity (dPa · s) |  | 861 | 1093 | 1280 | 690 |
| High temperature stability | Viscosity after stored at 60° C. (dPa · s) |  | 761 | 834 | 1416 | 989 |
|  | Ratio of viscosity after stored at 60° C./initial viscosity |  | 0.9 | 0.8 | 1.1 | 1.4 |
|  | Viscosity stability |  | b | b | b | b |
|  | Emulsification stability |  | b | b | b | c |
| Feeling on use | Lastingness of moist feeling |  | 4 | 2 | 2 | 2 |
|  | Thickness when applied |  | 4 | 2 | 2 | 2 |
|  | Skin-protecting feeling |  | 4 | 2 | 2 | 2 |
|  | Absence of friction when applied |  | 4 | 2 | 3 | 2 |
|  | Smoothness of skin |  | 4 | 3 | 2 | 2 |

The invention claimed is:

1. A W/O emulsion composition, comprising the following components (A), (B), (C), (D) and (E):
   (A) a glycerol monofatty acid ester having 12 to 26 carbon atoms;
   (B) a higher alcohol having 10 to 22 carbon atoms;
   (C) a ceramide;
   (D) at least one selected from the group consisting of sphingosine, a salt thereof, and an ionic surfactant; and
   (E) a nonionic surfactant comprising the following components (e1) and (e2):
   (e1) at least one selected from the group consisting of a crosslinked polyether-modified silicone and a crosslinked polyglycerol-modified silicone; and (e2) at least one selected from the group consisting of a polyether-modified silicone, a polyglycerol-modified silicone and a polyglycerol fatty acid ester.

2. The W/O emulsion composition according to claim 1, wherein a content of the component (e1) is 0.1% by mass or more and 10% by mass or less relative to a total mass of the W/O emulsion composition.

3. The W/O emulsion composition according to claim 1, wherein a mass ratio of a content of the component (e2) to a content of the component (e1), (e2/e1), is 0.1 or more and 10 or less.

4. The W/O emulsion composition according to claim 1, wherein an aqueous phase of the W/O emulsion composition comprises the components (A) to (D).

5. The W/O emulsion composition according to claim 1, wherein the component (D) is an anionic surfactant, and the W/O emulsion composition further comprises:
(F) a nonionic surfactant having an HLB of 8 or more that is not (e1) or (e2); and
(G) at least one selected from the group consisting of an inorganic acid and an organic acid having 6 or less carbon atoms.

6. The W/O emulsion composition according to claim 5, wherein a mass ratio of the component (F) to the component (G), (F/G), is 0.3 or more and 6.0 or less.

7. The W/O emulsion composition according to claim wherein a mass ratio of the component (F) to the component (A), (F/A), is 0.1 or more and 1.5 or less.

8. The W/O emulsion composition according to claim wherein an aqueous phase of the W/O emulsion composition comprises the components (A) to (D), (F) and (G).

9. A W/O emulsion composition, comprising the following components (A), (B), (C), (D) and (E):
(A) a glycerol monofatty acid ester having 12 to 26 carbon atoms;
(B) a higher alcohol having 10 to 22 carbon atoms;
(C) a ceramide;
(D) at least one anionic surfactant; and
(E) a nonionic surfactant comprising the following components (e1) and (e2):
(e1) at least one selected from the group consisting of a crosslinked polyether-modified silicone and a crosslinked polyglycerol-modified silicone; and
(e2) at least one selected from the group consisting of a polyether-modified silicone, a polyglycerol-modified silicone and a polyglycerol fatty acid ester,
wherein the W/O emulsion composition further comprises:
(F) a nonionic surfactant having an HLB of 8 or more; and
(G) at least one selected from the group consisting of an inorganic acid and an organic acid having 6 or less carbon atoms,
wherein a mass ratio of the component (F) to the component (G), (F/G), is 0.3 or more and 6.0 or less.

10. The W/O emulsion composition according to claim 9, wherein a mass ratio of the component (F) to the component (G), (F/G), is 1.0 or more and 5.0 or less.

11. The W/O emulsion composition according to claim 9, wherein a mass ratio of the component (F) to the component (A), (F/A), is 0.25 or more and 1.0 or less.

12. An O1/W/O emulsion cosmetic composition, comprising the following components (A), (B), (C), (D), (E), (F) and (G):
(A) at least one selected from the group consisting of glycerol monobehenate, glycerol monostearate and glycerol monopalmitate;
(B) at least one selected from the group consisting of stearyl alcohol, cetyl alcohol and behenyl alcohol;
(C) a ceramide;
(D) at least one selected from the group consisting of N-acylglutamate having 12 to 22 carbon atoms, and a salt thereof, and N-alkyloyl methyl taurate having 12 to 22 carbon atoms;
(E) a nonionic surfactant comprising the following components (e1) and (e2):
(e1) at least one selected from the group consisting of a crosslinked polyether-modified silicone and a crosslinked polyglycerol-modified silicone; and
(e2) at least one selected from the group consisting of a polyether-modified silicone, polyglycerol-modified silicone and polyglycerol fatty acid ester;
(F) a nonionic surfactant having an HLB of 8 or more and 20 or less that is not (e1) or (e2); and
(G) at least one selected from the group consisting of an inorganic acid and an organic acid having 6 or less carbon atoms,
wherein:
an inner oil phase O1 is dispersed in an aqueous phase of the O1/W/O emulsion cosmetic composition; and
the inner oil phase O1 comprises the components (A) to (D), and (F).

13. The O1/W/O emulsion cosmetic composition according to claim 12, wherein:
a content of the component (A) is from 0.2 to 10% by mass;
a content of the component (B) is from 0.2 to 10% by mass;
a content of the component (C) is from 0.5 to 10% by mass;
a content of the component (D) is from 0.05 to 5% by mass;
a content of the component (e1) is 0.1% by mass or more and 10% by mass or less;
a content of the component (e2) is 0.1% by mass or more and 10% by mass or less;
a content of the component (F) is from 0.05 to 1% by mass; and
a content of the component (G) is from 0.01 to 2% by mass, each relative to a total mass of the O1/W/O emulsion cosmetic composition.

14. The O1/W/O emulsion cosmetic composition according to claim 12, wherein:
a content of the component (A) is from 0.5 to 1.0% by mass;
a content of the component (B) is from 0.5 to 1.0% by mass;
a content of the component (C) is from 0.8 to 5% by mass;
a content of the component (D) is from 0.4 to 2% by mass;
a content of the component (e1) is 0.75% by mass or more and 1.5% by mass or less;
a content of the component (e2) is 3% by mass or more and 4% by mass or less;
a content of the component (F) is from 0.2 to 0.7% by mass; and
a content of the component (G) is from 0.1 to 0.2% by mass, each relative to a total mass of the O1/W/O emulsion cosmetic composition.

15. An O1/W/O emulsion cosmetic composition, comprising the following components (A), (B), (C), (D), (E), (F) and (G):
(A) a glycerol monofatty acid ester having 12 to 26 carbon atoms;

(B) a higher alcohol having 10 to 22 carbon atoms:
(C) a ceramide;
(D) N-alkyloyl methyl taurate having 16 to 20 carbon atoms;
(E) a nonionic surfactant comprising the following components (e1) and (e2):
 (e1) at least one selected from the group consisting of a crosslinked polyether-modified silicone and a crosslinked polyglycerol-modified silicone; and
 (e2) at least one selected from the group consisting of a polyether-modified silicone, polyglycerol-modified silicone and polyglycerol fatty acid ester;
(F) a nonionic surfactant having an HLB of 14 or more and 20 or less that is not (e1) or (e2); and
(G) at least one organic or inorganic acids selected from the group consisting of malic acid, lactic acid, citric acid, succinic acid, glutamic acid, adipic acid and phosphoric acid,
wherein:
an inner oil phase O1 is dispersed in an aqueous phase of the O1/W/O emulsion cosmetic composition; and
the inner oil phase O1 comprises the components (A) to (D), and (F).

* * * * *